United States Patent
Jacobs et al.

(12)

(10) Patent No.: US 8,574,565 B2
(45) Date of Patent: Nov. 5, 2013

(54) PHARMACEUTICAL COMPOSITION TO PROTECT AN ANIMAL AGAINST A DISORDER ARISING FROM AN INFECTION WITH A BACTERIUM THAT BELONGS TO THE GROUP OF NOCARDIOFORM ACTINOMYCETES

(75) Inventors: Antonius Arnoldus Christiaan Jacobs, Boxmeer (NL); Robert Van Der Geize, Haren (NL); Lubbert Dijkhuizen, Haren (NL)

(73) Assignee: Intervet International B.V., Boxmeer (NL)

( * ) Notice: Subject to any disclaimer, the term of this patent is extended or adjusted under 35 U.S.C. 154(b) by 67 days.

(21) Appl. No.: 13/144,042

(22) PCT Filed: Jan. 11, 2010

(86) PCT No.: PCT/EP2010/050196
§ 371 (c)(1),
(2), (4) Date: Jul. 11, 2011

(87) PCT Pub. No.: WO2010/079224
PCT Pub. Date: Jul. 15, 2010

(65) Prior Publication Data
US 2011/0274660 A1    Nov. 10, 2011

Related U.S. Application Data

(60) Provisional application No. 61/143,869, filed on Jan. 12, 2009.

(30) Foreign Application Priority Data

Jan. 12, 2009 (EP) .................................... 09150379

(51) Int. Cl.
*A61K 35/74* (2006.01)
*C12N 1/20* (2006.01)
*A61P 31/04* (2006.01)

(52) U.S. Cl.
USPC ...................................... 424/93.2; 435/252.1

(58) Field of Classification Search
None
See application file for complete search history.

(56) References Cited

U.S. PATENT DOCUMENTS

2009/0186390 A1 *   7/2009   van der Geize et al. ...... 435/127

FOREIGN PATENT DOCUMENTS

| WO | WO99/05304 | 2/1999 |
| WO | WO2008/070039 | 6/2008 |

OTHER PUBLICATIONS

International Search Report corresponding to PCT/EP2010/050196, mailed on Mar. 19, 2010.
Anes et al., "Dynamic life and death interactions between *Mycobacterium smegmatis* and J774 macrophages", Cellular Microbiology, 2006, pp. 939-960, vol. 8(6).
Sekine et al., "Sequence analysis of three plasmids harboured in *Rhodococcus erythropolis* strain PR4", Environmental Microbiology, 2006, pp. 334-346, vol. 8(2).

* cited by examiner

*Primary Examiner* — Scott Long

(57) ABSTRACT

The invention pertains to a pharmaceutical composition to protect an animal against a disorder arising from an infection with a bacterium that belongs to the group of nocardioform actinomycetes having the ability to survive within macrophages of the animal, comprising live bacteria of a nocardioform actinomycetes species, the live bacteria being attenuated by inactivation of a gene that encodes a protein involved in methylhexahydroindanedione propionate degradation, and a pharmaceutically acceptable carrier for these live bacteria.

3 Claims, 4 Drawing Sheets

SEQUENCE LISTING

<160> NUMBER OF SEQ ID NOS: 59

<210> SEQ ID NO 1
<211> LENGTH: 296
<212> TYPE: PRT
<213> ORGANISM: Rhodococcus equi

<400> SEQUENCE: 1

```
Met Ala Glu Lys Arg Asp Lys Arg Ser Leu Asp Glu Ala Val Ala
1               5                   10                  15

Gly Ile Gln Ser Gly Met Thr Ile Gly Ile Gly Trp Gly Ser Arg
            20                  25                  30

Arg Lys Pro Met Ala Leu Val Arg Ala Leu Leu Arg Ser Asp Val Lys
        35                  40                  45

Asp Leu Thr Val Val Gly Tyr Leu Gly Pro Asp Leu Gly Leu Leu Ile
    50                  55                  60

Ser Ala Gly Lys Val Lys Arg Ala Tyr Tyr Gly Phe Val Ser Leu Asp
65                  70                  75                  80

Ser Ala Pro Phe Tyr Asp Pro Trp Phe Ala Gln Ala Arg Val Ala Gly
            85                  90                  95

Thr Ile Glu Ser Arg Glu Met Asp Glu Gly Met Val Lys Ala Gly Leu
            100                 105                 110

Gln Ala Ala Ala Arg Leu Pro Phe Met Pro Ile Arg Ala Gly Leu
        115                 120                 125

Gly Ser Asp Ala Gln Thr Val Trp Gly Asp Glu Leu Lys Thr Val Ala
    130                 135                 140

Ser Pro Tyr Pro Asp Ala Asp Gly Arg Thr Glu Thr Leu Ile Ala Met
145                 150                 155                 160

Pro Ala Leu Lys Leu Asp Ala Ala Leu Val His Leu Asp Leu Ala Asp
            165                 170                 175

Glu Arg Gly Asn Ala Ala Tyr Thr Gly Val Asp Pro Tyr Phe Asp Asp
            180                 185                 190

Leu Phe Cys Leu Ala Ala Glu Gln Arg Ile Leu Ser Ala Asp Lys Ile
        195                 200                 205

Val Ser Thr Glu Glu Leu Val Lys Ser Val Pro Asn Gln Ala Leu Ile
210                 215                 220

Leu Asn Arg Ser Met Val Asp Thr Val Thr Glu Ala Pro Asn Gly Ala
225                 230                 235                 240

His Phe Thr Phe Ala Gly Ser Tyr Lys Arg Asp Glu Lys Phe Gln Arg
            245                 250                 255

His Tyr Ala Glu Ser Ala Lys Thr Pro Glu Ala Trp Gln Ala Phe Ala
            260                 265                 270

Asp Thr Tyr Leu Ser Gly Ser Glu Asp Tyr Gln Ala Ala Val Arg
        275                 280                 285

Lys Phe Ala Glu Glu Gln Lys Ser
        290                 295

<210> SEQ ID NO 2
<211> LENGTH: 249
<212> TYPE: PRT
<213> ORGANISM: Rhodococcus equi

<400> SEQUENCE: 2

Met Thr Glu Val Thr Arg Ala Glu Tyr Cys Ala Val Ala Cys Ala Glu
1               5                   10                  15

Leu Phe Ala Asp Ala Gly Glu Ile Phe Ala Ser Pro Met Ala Thr Leu
            20                  25                  30

Pro Leu Ile Gly Ala Arg Leu Ala Lys Leu Thr Thr Glu Pro Asp Leu
        35                  40                  45

Ile Ile Thr Asp Gly Glu Ala Leu Ile Leu Ala Glu Ala Pro Ala Ile
    50                  55                  60

Gly Ala Ser Ala Pro Ile Glu Gly Tyr Ile Pro Phe Ser Lys Val Phe
65                  70                  75                  80
```

-continued

Asp Val Val Ala Ser Gly Arg Arg His Val Met Gly Ala Asn Gln
            85                  90                  95

Ile Asp Lys Tyr Gly Asn Gln Asn Leu Ser Ala Phe Gly Pro Leu Asp
                100                 105                 110

Lys Pro Thr Arg Gln Met Phe Gly Leu Arg Gly Ala Pro Gly Asn Thr
            115                 120                 125

Ile Asn His Ala Thr Ser Tyr Trp Val Gly Lys His Ser Ser Arg Val
130                 135                 140

Phe Ala Glu Lys Val Asp Val Val Cys Gly Val Gly Tyr Asp Lys Val
145                 150                 155                 160

Asp Pro Glu Asn Pro Ala Phe Arg Phe Leu Lys Asn His Arg Val Val
                165                 170                 175

Thr Asn Leu Gly Val Phe Asp Phe Gln Gly Pro Gly Gln Thr Met Arg
            180                 185                 190

Ala Val Thr Leu His Pro Gly Val Thr Ala Glu Asp Val Lys Ala Asn
            195                 200                 205

Thr Ser Phe Glu Ile Ala Asp Leu Asp Ser Ala Gly Val Thr Arg Glu
210                 215                 220

Pro Thr Ala Glu Glu Leu Arg Leu Ile Arg Glu Val Ile Asp Pro Lys
225                 230                 235                 240

Ser Leu Arg Asp Arg Glu Val Ser Ala
                245

<210> SEQ ID NO 3
<211> LENGTH: 287
<212> TYPE: PRT
<213> ORGANISM: Rhodococcus equi

<400> SEQUENCE: 3

Leu Ser Asp Lys Arg Met Ser Glu Lys Glu Val Val Gly Arg Leu Arg
1               5                   10                  15

Ser Gly Met Thr Ile Gly Ile Gly Gly Trp Gly Ser Arg Arg Lys Pro
            20                  25                  30

Met Ser Leu Val Arg Glu Ile Leu Arg Ser Asp Leu Asp Asp Leu Thr
            35                  40                  45

Val Val Ser Tyr Gly Gly Pro Asp Val Gly Leu Leu Cys Ala Ala Gly
50                  55                  60

Lys Val Arg Lys Val Val Phe Gly Phe Val Ser Leu Asp Ser Ile Pro
65                  70                  75                  80

Leu Asp Pro His Phe Arg Ala Ala Arg Gln Gly Gly Arg Val Glu Val
                85                  90                  95

Ala Glu Tyr Asp Glu Gly Met Leu Gln Trp Gly Leu Tyr Ala Ala Gly
                100                 105                 110

Ile Arg Leu Pro Tyr Leu Pro Thr Arg Ala Gly Leu Gly Ser Asp Val
            115                 120                 125

Met Arg Val Asn Pro Glu Leu Arg Thr Val Thr Asp Pro Tyr Gly Asp
130                 135                 140

Glu Thr Leu Val Ala Met Pro Ala Ile Pro Leu Asp Ala Ala Leu Val
145                 150                 155                 160

His Met Asn Arg Ala Asp Val His Gly Asn Ala Gln Tyr Leu Gly Pro
                165                 170                 175

Asp Leu Tyr Phe Asp Asp Leu Phe Cys Met Ala Ala Glu Gln Val Tyr
                180                 185                 190

Val Ser Cys Glu Arg Ile Val Pro Thr Ala Glu Leu Thr Ala Asp Ala
            195                 200                 205

```
His Pro Ser Thr Ile Arg Ile Pro Arg Leu Leu Val Ser Gly Val Val
    210                 215                 220

Ala Ala Pro Gly Gly Ala His Phe Thr Ser Cys Val Pro Asp Tyr Ala
225                 230                 235                 240

Arg Asp Glu Ala Phe Gln Arg Glu Tyr Val Thr Ala Ala Lys Asp Pro
                245                 250                 255

Glu Lys Trp Gln Ala Phe Val Asp Arg Tyr Leu Ala Val Pro Glu Ala
                260                 265                 270

Glu Tyr Gln Arg Ala Val Arg Gly Ala Arg Glu Glu Ala Ser Ala
                275                 280                 285

<210> SEQ ID NO 4
<211> LENGTH: 252
<212> TYPE: PRT
<213> ORGANISM: Rhodococcus equi

<400> SEQUENCE: 4

Met Ser Ala Ala Thr Arg Ala Glu Val Cys Ala Val Cys Ala Glu
1               5                  10                  15

Ala Tyr Arg Gly Asn Gly Glu Val Ile Ala Ser Ala Phe Gly Thr Ile
                20                  25                  30

Pro Ala Ile Gly Val Arg Leu Ala Arg His Thr Phe Glu Pro Asp Leu
                35                  40                  45

Val Val Ser Asp Gly Glu Ala Ala Val Arg Gly Thr Trp Ala Val
    50                  55                  60

Gly Gly Pro Ala Asp Gly Glu Val Glu Ala Trp Leu Pro Phe Asn Gln
65                  70                  75                  80

Ile Phe Asp Leu Val Trp Asn Gly Lys Arg His Ile Met Met Ile Pro
                85                  90                  95

Thr Gln Leu Asp Thr Tyr Gly Asn Cys Asn Ile Ser Ala Ile Gly Asp
                100                 105                 110

His Asp Arg Pro Ser Val Gln Leu Leu Gly Val Arg Gly Ala Pro Gly
                115                 120                 125

Asn Thr Val Tyr His Pro Thr Ser Tyr Trp Val Pro Lys His Ser Thr
130                 135                 140

Arg Val Phe Val Pro Lys Val Asp Met Val Ser Gly Val Gly Asn Asp
145                 150                 155                 160

Asn Ala Arg Lys Ala Gly Pro Ala Ala Thr Arg Tyr His Glu Leu Arg
                165                 170                 175

Arg Val Val Thr Asp Leu Ala Val Leu Asp Phe Thr Pro Asp Ser Gly
                180                 185                 190

Arg Leu Arg Leu Val Ser Val His Pro Gly Val Thr Val Asp Val
                195                 200                 205

Val Ala Ala Thr Gly Phe Asp Leu Val Ile Pro Asp Ser Val Pro Gln
210                 215                 220

Thr Arg Ala Pro Ser Ala Glu Glu Leu Glu Leu Ile Arg Thr Val Ile
225                 230                 235                 240

Asp Pro Arg Asn Leu Arg Asp Lys Glu Val Pro Ala
                245                 250

<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
```

```
tgccgctgac ggaggagatc at                                         22

<210> SEQ ID NO 6
<211> LENGTH: 28
<212> TYPE: DNA
<213> ORGANISM: Artificial
<220> FEATURE:
<223> OTHER INFORMATION: primer

<400> SEQUENCE: 6
gatatcatac cggcgactgc ctcatcca                                   28

<210> SEQ ID NO 7
<211> LENGTH: 27
<212> TYPE: DNA
<213> ORGANISM: Artificial
<220> FEATURE:
<223> OTHER INFORMATION: primer

<400> SEQUENCE: 7
gatatcgaac cacccgtggt caccaac                                    27

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
tcgagcagcg aactggcctg aa                                         22

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
agtccgacga cgatcgagtt ga                                         22

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
tcacgccgag acctcacggt ca                                         22

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
atggctgaga agcgcgacaa gc                                         22

<210> SEQ ID NO 12
<211> LENGTH: 22
<212> TYPE: DNA
<213> ORGANISM: Artificial
```

```
<220> FEATURE:
<223> OTHER INFORMATION: primer

<400> SEQUENCE: 12
tcgtcgtcgt ctcgcaccag at                                              22

<210> SEQ ID NO 13
<211> LENGTH: 22
<212> TYPE: DNA
<213> ORGANISM: Artificial
<220> FEATURE:
<223> OTHER INFORMATION: primer

<400> SEQUENCE: 13
atggctgaga agcgcgacaa gc                                              22

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
tcacgccgag acctcacggt ca                                              22

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15
tcgaggtggt tcatgacgaa ga                                              22

<210> SEQ ID NO 16
<211> LENGTH: 28
<212> TYPE: DNA
<213> ORGANISM: Artificial
<220> FEATURE:
<223> OTHER INFORMATION: primer

<400> SEQUENCE: 16
agatctccgg ccgaccacct ctttctcc                                        28

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
agatctagtg cggaggagct ggaactga                                        28

<210> SEQ ID NO 18
<211> LENGTH: 27
<212> TYPE: DNA
<213> ORGANISM: Artificial
<220> FEATURE:
<223> OTHER INFORMATION: primer

<400> SEQUENCE: 18
actagtgatc tcgtccgtga cctgatg                                         27
```

```
<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
ccgacatcac ggtgtcggga tc                                              22

<210> SEQ ID NO 20
<211> LENGTH: 22
<212> TYPE: DNA
<213> ORGANISM: Artificial
<220> FEATURE:
<223> OTHER INFORMATION: primer

<400> SEQUENCE: 20
tcacgcggga acctccttgt cg                                              22

<210> SEQ ID NO 21
<211> LENGTH: 22
<212> TYPE: DNA
<213> ORGANISM: Artificial
<220> FEATURE:
<223> OTHER INFORMATION: primer

<400> SEQUENCE: 21
ttgtcggaca agagaatgtc gg                                              22

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
ggtcgtgacg tccgcggtgt tc                                              22

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
ttgtcggaca agagaatgtc gg                                              22

<210> SEQ ID NO 24
<211> LENGTH: 22
<212> TYPE: DNA
<213> ORGANISM: Artificial
<220> FEATURE:
<223> OTHER INFORMATION: primer

<400> SEQUENCE: 24
tcacgcggga acctccttgt cg                                              22

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
```
gcagcagtgc gattctcaat ag                                                 22

<210> SEQ ID NO 26
<211> LENGTH: 22
<212> TYPE: DNA
<213> ORGANISM: Artificial
<220> FEATURE:
<223> OTHER INFORMATION: primer

<400> SEQUENCE: 26
taactccacc ggactggata tg                                                 22

<210> SEQ ID NO 27
<211> LENGTH: 22
<212> TYPE: DNA
<213> ORGANISM: Artificial
<220> FEATURE:
<223> OTHER INFORMATION: primer

<400> SEQUENCE: 27
ttcgagatgg ccgcgatcga at                                                 22

<210> SEQ ID NO 28
<211> LENGTH: 28
<212> TYPE: DNA
<213> ORGANISM: Artificial
<220> FEATURE:
<223> OTHER INFORMATION: primer

<400> SEQUENCE: 28
actagtgatg gtcatgccgc tctcgata                                           28

<210> SEQ ID NO 29
<211> LENGTH: 28
<212> TYPE: DNA
<213> ORGANISM: Artificial
<220> FEATURE:
<223> OTHER INFORMATION: primer

<400> SEQUENCE: 29
actagtcagg tcgccgacaa cacctcgt                                           28

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30
aagcttgaat tcgtcgccga cggtgaag                                           28

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
acgccagcta ccgcatggaa                                                    20

<210> SEQ ID NO 32
<211> LENGTH: 20
<212> TYPE: DNA
<213> ORGANISM: Artificial

-continued

<220> FEATURE:
<223> OTHER INFORMATION: primer

<400> SEQUENCE: 32
atcacctcgc gcagcagctt                                              20

<210> SEQ ID NO 33
<211> LENGTH: 22
<212> TYPE: DNA
<213> ORGANISM: Artificial
<220> FEATURE:
<223> OTHER INFORMATION: Primer

<400> SEQUENCE: 33
tccattcgcg ccagcgcatt ct                                           22

<210> SEQ ID NO 34
<211> LENGTH: 25
<212> TYPE: DNA
<213> ORGANISM: Artificial
<220> FEATURE:
<223> OTHER INFORMATION: Primer

<400> SEQUENCE: 34
agatctcttc gagccattcg cgaat                                        25

<210> SEQ ID NO 35
<211> LENGTH: 25
<212> TYPE: DNA
<213> ORGANISM: Artificial
<220> FEATURE:
<223> OTHER INFORMATION: Primer

<400> SEQUENCE: 35
agatctacgg cggatccaac gagat                                        25

<210> SEQ ID NO 36
<211> LENGTH: 22
<212> TYPE: DNA
<213> ORGANISM: Artificial
<220> FEATURE:
<223> OTHER INFORMATION: Primer

<400> SEQUENCE: 36
aggtcgcgga actcctggtt ac                                           22

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
acgatgtacg cacgaccgac ct                                           22

<210> SEQ ID NO 38
<211> LENGTH: 22
<212> TYPE: DNA
<213> ORGANISM: Artificial
<220> FEATURE:
<223> OTHER INFORMATION: Primer

<400> SEQUENCE: 38
gacagcttct cgacggtctc ac                                           22

-continued

```
<210> SEQ ID NO 39
<211> LENGTH: 22
<212> TYPE: DNA
<213> ORGANISM: Artificial
<220> FEATURE:
<223> OTHER INFORMATION: Primer

<400> SEQUENCE: 39
aggcgaggcg gaacctctat ac                                              22

<210> SEQ ID NO 40
<211> LENGTH: 22
<212> TYPE: DNA
<213> ORGANISM: Artificial
<220> FEATURE:
<223> OTHER INFORMATION: Primer

<400> SEQUENCE: 40
cgtccagaac gatggagagg ta                                              22

<210> SEQ ID NO 41
<211> LENGTH: 22
<212> TYPE: DNA
<213> ORGANISM: Artificial
<220> FEATURE:
<223> OTHER INFORMATION: Primer

<400> SEQUENCE: 41
aggcgaggcg gaacctctat ac                                              22

<210> SEQ ID NO 42
<211> LENGTH: 22
<212> TYPE: DNA
<213> ORGANISM: Artificial
<220> FEATURE:
<223> OTHER INFORMATION: Primer

<400> SEQUENCE: 42
gacagcttct cgacggtctc ac                                              22

<210> SEQ ID NO 43
<211> LENGTH: 403
<212> TYPE: PRT
<213> ORGANISM: Rhodococcus equi

<400> SEQUENCE: 43
```

Val Asp Val Ser Gln Gly Ile Glu Thr Ser Glu Gln Ala Ala Ala Asp
1               5                   10                  15

Glu Ala Phe Ala Arg Glu Ile Arg Glu Trp Leu Glu Glu Asn Leu Ser
            20                  25                  30

Gly Lys Phe Ala Glu Leu Lys Gly Leu Gly Gly Pro Gly Arg Glu His
        35                  40                  45

Glu Ala Phe Glu Glu Arg Leu Glu Trp Asp Arg His Leu Ala Ala Ala
    50                  55                  60

Gly Trp Thr Cys Leu Gly Trp Pro Lys Glu Tyr Gly Gly Arg Glu Ala
65                  70                  75                  80

Thr Leu Ser Gln Gln Ile Ile Phe His Gln Glu Tyr Ala Arg Ala Asn
                85                  90                  95

Ala Pro Ala Arg Val Ser His Ile Gly Glu Glu Leu Leu Gly Pro Thr
            100                 105                 110

Leu Ile Ala Phe Gly Thr Glu Glu Gln Lys Gln Arg Phe Leu Pro Gly
        115                 120                 125

Ile Lys Thr Val Thr Glu Leu Trp Cys Gln Gly Tyr Ser Glu Pro Gly

```
            130                 135                 140
Ala Gly Ser Asp Leu Ala Asn Val Ser Thr Thr Ala Arg Leu Asp Gly
145                 150                 155                 160

Asp Gln Trp Val Val Asn Gly Gln Lys Val Trp Thr Ser Leu Ala His
                165                 170                 175

Leu Ala Asp Trp Cys Phe Val Val Ala Arg Thr Glu Pro Gly Ser Ser
                180                 185                 190

Arg His Lys Gly Leu Ser Tyr Leu Val Pro Met Asn Gln Glu Gly
                195                 200                 205

Val Glu Val Arg Pro Ile Ile Gln Leu Thr Gly Thr Ser Glu Phe Asn
210                 215                 220

Glu Val Phe Phe Asp Asn Ala Arg Thr Asp Ala Asp Leu Val Val Gly
225                 230                 235                 240

Gly Glu Gly Asn Gly Trp Gly Thr Ala Met Gly Thr Leu Thr Phe Glu
                245                 250                 255

Arg Gly Val Ser Thr Leu Gly Gln Gln Ile Gly Phe Ala Arg Glu Leu
                260                 265                 270

Glu Ser Ile Val Glu Leu Ala Glu Arg Asn Gly Ala Ala Glu Asn Pro
275                 280                 285

Ala Ile Arg Asn Lys Ile Ser Arg Ala Trp Thr Ser Leu Gln Val Ile
290                 295                 300

Arg Ala His Ala Leu Arg Thr Leu Ala Ser Val Asp Ala Ser Ala Asn
305                 310                 315                 320

Gly Gly Glu Ala Ser Val Ala Lys Leu Leu Trp Ala Asn Trp His Arg
                325                 330                 335

Gly Leu Gly Glu Leu Ala Met Glu Val Gln Gly Ala Ala Ser Leu Ile
                340                 345                 350

Gly Val Glu Asn Thr Glu Pro Gly Glu Glu Leu Asn Asp Leu Gln Arg
                355                 360                 365

Leu Trp Leu Phe Thr Arg Ala Asp Thr Ile Tyr Gly Gly Ser Asn Glu
370                 375                 380

Ile Gln Arg Asn Ile Ile Ala Glu Arg Val Leu Gly Leu Pro Arg Glu
385                 390                 395                 400

Ala Arg Pro

<210> SEQ ID NO 44
<211> LENGTH: 22
<212> TYPE: DNA
<213> ORGANISM: Artificial
<220> FEATURE:
<223> OTHER INFORMATION: Primer

<400> SEQUENCE: 44
gtggtcgttc gccgccgccg tg                                          22

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
cgatgccgat ggtcatgccg ct                                          22

<210> SEQ ID NO 46
<211> LENGTH: 26
<212> TYPE: DNA
```

<210> SEQ ID NO 47
<211> LENGTH: 35
<212> TYPE: DNA
<213> ORGANISM: Artificial
<220> FEATURE:
<223> OTHER INFORMATION: Primer

<400> SEQUENCE: 46
ggcaaccaga acctctccgc cttcgg                                          26

<210> SEQ ID NO 47
<211> LENGTH: 35
<212> TYPE: DNA
<213> ORGANISM: Artificial
<220> FEATURE:
<223> OTHER INFORMATION: Primer

<400> SEQUENCE: 47
gtgttgccct cgaccaggcc ggcgcgcaac agcat                                35

<210> SEQ ID NO 48
<211> LENGTH: 22
<212> TYPE: DNA
<213> ORGANISM: Artificial
<220> FEATURE:
<223> OTHER INFORMATION: Primer

<400> SEQUENCE: 48
agcggcatga ccatcggcat cg                                              22

<210> SEQ ID NO 49
<211> LENGTH: 26
<212> TYPE: DNA
<213> ORGANISM: Artificial
<220> FEATURE:
<223> OTHER INFORMATION: Primer

<400> SEQUENCE: 49
ccgaaggcgg agaggttctg gttgcc                                          26

<210> SEQ ID NO 50
<211> LENGTH: 23
<212> TYPE: DNA
<213> ORGANISM: Artificial
<220> FEATURE:
<223> OTHER INFORMATION: Primer

<400> SEQUENCE: 50
atgcgcgaca agcgaatgag cct                                             23

<210> SEQ ID NO 51
<211> LENGTH: 22
<212> TYPE: DNA
<213> ORGANISM: Artificial
<220> FEATURE:
<223> OTHER INFORMATION: Primer

<400> SEQUENCE: 51
tcatgccgtc acttccttcc cg                                              22

<210> SEQ ID NO 52
<211> LENGTH: 22
<212> TYPE: DNA
<213> ORGANISM: Artificial
<220> FEATURE:
<223> OTHER INFORMATION: Primer

<400> SEQUENCE: 52
tcctcgtcgc cgtagtgcag gt                                              22

```
<210> SEQ ID NO 53
<211> LENGTH: 27
<212> TYPE: DNA
<213> ORGANISM: Artificial
<220> FEATURE:
<223> OTHER INFORMATION: Primer

<400> SEQUENCE: 53
cccgggatgg tcatgccgct gcggagc                                               27

<210> SEQ ID NO 54
<211> LENGTH: 22
<212> TYPE: DNA
<213> ORGANISM: Artificial
<220> FEATURE:
<223> OTHER INFORMATION: Primer

<400> SEQUENCE: 54
cccgggtgtg tccgccgacg ag                                                    22

<210> SEQ ID NO 55
<211> LENGTH: 22
<212> TYPE: DNA
<213> ORGANISM: Artificial
<220> FEATURE:
<223> OTHER INFORMATION: Primer

<400> SEQUENCE: 55
ttggcggcca tgatgacctg gg                                                    22

<210> SEQ ID NO 56
<211> LENGTH: 23
<212> TYPE: DNA
<213> ORGANISM: Artificial
<220> FEATURE:
<223> OTHER INFORMATION: Primer

<400> SEQUENCE: 56
atgcgcgaca agcgaatgag cct                                                   23

<210> SEQ ID NO 57
<211> LENGTH: 22
<212> TYPE: DNA
<213> ORGANISM: Artificial
<220> FEATURE:
<223> OTHER INFORMATION: Primer

<400> SEQUENCE: 57
gccttccacc agaccggctt tg                                                    22

<210> SEQ ID NO 58
<211> LENGTH: 291
<212> TYPE: PRT
<213> ORGANISM: Nocardia seriolae

<400> SEQUENCE: 58
```

Met Arg Asp Lys Arg Met Ser Leu Asp Glu Val Val Gly Glu Leu Arg
1               5                   10                  15

Ser Gly Met Thr Ile Gly Ile Gly Gly Trp Gly Ser Arg Arg Lys Pro
            20                  25                  30

Met Ala Phe Val Arg Ala Leu Leu Arg Ser Asp Leu Lys Asp Leu Thr
        35                  40                  45

Val Val Thr Tyr Gly Gly Pro Asp Leu Gly Leu Leu Cys Ser Ala Gly
    50                  55                  60

```
Lys Val Arg Lys Ala Tyr Tyr Gly Phe Val Ser Leu Asp Ser Ala Pro
 65                  70                  75                  80

Phe Tyr Asp Pro Trp Phe Ala Lys Ala Arg Thr Glu Gly Ala Ile Thr
                 85                  90                  95

Val Arg Glu Met Asp Glu Gly Met Val Lys Cys Gly Leu Gln Ala Ala
            100                 105                 110

Ala Ala Arg Leu Pro Phe Leu Pro Ile Arg Ala Gly Leu Gly Ser Ala
        115                 120                 125

Val Ile Asp Phe Trp Glu Gly Glu Leu Lys Thr Val Gln Ser Pro Tyr
130                 135                 140

Pro Thr Asp Gly Lys Thr Glu Thr Leu Val Ala Met Pro Ala Leu Asn
145                 150                 155                 160

Leu Asp Ala Ala Phe Val His Leu Asp Leu Gly Asp Lys His Gly Asn
                165                 170                 175

Ala Ala Tyr Thr Gly Val Asp Pro Tyr Met Asp Asp Leu Tyr Met Leu
            180                 185                 190

Ser Ala Glu Lys Arg Tyr Leu Ser Val Asp Arg Leu Val Glu Thr Glu
        195                 200                 205

Glu Leu Val Lys Ala Val Pro Thr Gln Ala Leu Ile Leu Asn Arg Met
210                 215                 220

Met Val Asp Gly Val Val Glu Ala Pro Gly Gly Ala His Phe Thr Phe
225                 230                 235                 240

Ser Gly Ser Tyr Gly Arg Asp Glu Lys Phe Gln Arg His Tyr Val Glu
                245                 250                 255

Ala Ala Lys Thr Pro Glu Ser Trp Ala Glu Phe Lys Ala Arg Tyr Leu
            260                 265                 270

Asp Val Ser Glu Asp Gly Tyr Gln Ala Ala Val Glu Ala Phe Ala Glu
        275                 280                 285

Glu Gln Lys
    290

<210> SEQ ID NO 59
<211> LENGTH: 252
<212> TYPE: PRT
<213> ORGANISM: Nocardia seriolae

<400> SEQUENCE: 59

Met Thr Asp Thr Ala Thr Val Thr Arg Ala Glu Ile Cys Val Val Ala
1               5                   10                  15

Ala Ala Glu Ile Phe Arg Gly Ala Gly Glu Ile Met Ala Ser Pro Met
            20                  25                  30

Ser Thr Val Thr Thr Ile Gly Ala Arg Leu Ala Arg Leu Thr Phe Glu
        35                  40                  45

Pro Asp Leu Leu Leu Ser Asp Gly Glu Ala Leu Phe Phe Ala Glu Val
50                  55                  60

Pro Pro Ile Gly Gly Lys Ala Pro Ile Glu Gly Trp Ile Pro Phe Ser
65                  70                  75                  80

Lys Val Phe Asp Val Val Asn Ser Gly Arg Arg His Val Val Met Gly
                85                  90                  95

Ala Asn Gln Leu Asp Arg Phe Gly Asn Gln Asn Leu Ser Ala Phe Gly
            100                 105                 110

Pro Leu Gln Gln Pro Thr Arg Gln Met Phe Gly Val Arg Gly Ala Pro
        115                 120                 125

Gly Asn Thr Ile Asn His Ala Thr Ser Tyr Phe Val Pro Lys His Asn
130                 135                 140
```

-continued

```
Lys Arg Val Phe Val Asp Gln Val Asp Ile Val Ser Gly Ile Gly Tyr
145                 150                 155                 160

Asp Lys Ile Asp Ser Glu Asn Pro Ala Tyr Arg Phe His His Leu His
                165                 170                 175

Arg Val Val Ser Asn Leu Gly Val Phe Asp Phe Asn Gly Pro Asp His
            180                 185                 190

Thr Met Arg Ala Leu Ser Leu His Pro Gly Val Ser Ala Asp Glu Val
        195                 200                 205

Ala Glu Asn Thr Leu Phe Glu Ile Ala Gly Leu Ala Glu Ala Gly Glu
    210                 215                 220

Thr Arg Leu Pro Thr Glu Glu Glu Leu Thr Ile Ile Arg Thr Val Leu
225                 230                 235                 240

Asp Pro Lys Gly Phe Arg Gly Lys Glu Val Thr Ala
                245                 250
```

PHARMACEUTICAL COMPOSITION TO PROTECT AN ANIMAL AGAINST A DISORDER ARISING FROM AN INFECTION WITH A BACTERIUM THAT BELONGS TO THE GROUP OF NOCARDIOFORM ACTINOMYCETES

CROSS-REFERENCE TO RELATED APPLICATIONS

This application is a national stage entry under 35 U.S.C. §371 of PCT/EP2010/050196 filed on Jan. 11, 2010, which claims priority to U.S. Provisional Application No. 61/143,869, filed on Jan. 12, 2009, and EP Application No. 09150379.7, filed on Jan. 12, 2009. The content of PCT/EP2010/050196 is hereby incorporated by reference in its entirety.

The present invention pertains to a pharmaceutical composition to protect an animal against a disorder arising from an infection with a bacterium that belongs to the group of nocardioform actinomycetes. The invention also pertains to the use of live attenuated bacteria of this group to manufacture the said composition and a method of treating an animal with this composition.

Within the bacteria of the class Actinobacteria there is an order of bacteria called Actinomycetales, commonly referred to as actinomycetes. Bacteria that belong to this order are filamentous gram positive bacteria (several species however have complex cell wall structures which makes classic gram staining less- or even unsuitable, as is for example the case with many species that belong to the Actinomycetales family Mycobacteriaceae) with a high G+C content. They are best known as soil dwelling organisms, although various strains inhabit plants and animals, including humans. They produce resistant spores which are often attached to aerial mycelium or hyphae. Actinomycetes play an important role in the decomposition of organic material. Several species are used in industry and pharma-research because of their typical properties.

Most actinomycetes are non-pathogenic for animals (the term animals used in connection with the present invention includes humans). However, within the many suborders of the actinomycetes (i.a. Streptosporangineae, Micrococcineae, Streptomycineae and Frankineae) there is one suborder, viz. the Corynebacterineae, which houses, next to a large amount of non-pathogenic bacteria, a substantial number of animal pathogens. It appears that these pathogens reside within the phylogenic group known as the nocardioform actinomycetes, which encompasses the families Mycobacteriaceae, Nocardiaceae and Corynebacteriaceae (see i.a. chapter 11, titled: *Rhodococus equi*: Pathogenesis and Replication in Macrophages, in "Opportunistic Intracellular Bacteria and Immunity", by Lois J. Paradise et al (eds.), New York, 1999). Remarkably, against the larger part of diseases related to infection with these pathogens there is hardly any adequate prophylactic treatment (i.e. treatment prior to, or essentially at the same time as exposure to the disease causing pathogen which may either be able to prevent the disease from being contracted, or at least mitigate the effects of the disease) available. During recent years the recognition that the families Mycobacteriaceae, Nocardiaceae and Corynebacteriaceae of the phylogenic group of nocardioform actinomycetes are very closely related families within the suborder of the Corynebacterineae, has been confirmed (see also University of California, San Diego, Outline of Senior Project, Marelle L. Yehuda, Jun. 2, 2005). It has also become clear that in particular the pathogenic bacteria in this group, at least the ones for which no adequate prophylactic treatment is available (such as for example *Mycobacterium tuberculosis, Nocardia seriolae* and *Rhodococcus equi*), have an important property in common: infection typically occurs via skin or mucous membrane, followed by dissemination of the bacteria within macrophages and replication within these macrophages (see i.a. Microbes and Infection 7, 2005, 1352-1363; Proceedings of the National Academy of Sciences, Jun. 7, 2005, Vol. 102, no 23, pp 8327-8332; Nature Medicine 13, 282-284, 2007; Transplantation Proceedings, Volume 36, Issue 5, June 2004, pp 1415-1418). Indeed macrophages are at the frontline of host immune defence against microbial infections, but unlike bacteria that depend on the avoidance of phagocytosis to survive in the host, the currently contemplated pathogenic bacteria within this group target macrophages to survive and even replicate in the host. The present invention is concerned with these bacteria that have the ability to survive within macrophages of an animal, and in connection with the current invention will be referred to as macrophage surviving nocardioform actinomycetes.

Apparently, the macrophage surviving nocardioform actinomycetes have evolved to evade critical functions of an animal's defence against microbes. In particular *Mycobacterium tuberculosis*, the causative microbe of tuberculosis, is a species that has successfully exploited macrophages as its primary niche in vivo, but other bacterial species that belong to the group of nocardioform actinomycetes, including Mycobacteriaceae, Nocardiaceae and Corynebacteriaceae, have adopted the same strategy. These are for example *Mycobacterium ulcerans* that causes Buruli ulcer, *Mycobacterium avium* paratuberculosis that causes Johne's disease in cattle and which is linked to Crohn's disease in humans, *Mycobacterium bovis* that causes bovine tuberculosis, *Mycobacterium avium* which is related to opportunistic infection of immunocompromised subjects such as AIDS-patients, *Nocardia seriolae* and *Nocardia farcinia* that cause nocardiosis in fish, *Nocardia asteroides* which causes infection in renal transplant recipients, *Rhodococcus equi* (formerly known as *Corynebacterium*) that causes pneumonia in foals and which is also connected to opportunistic infections in immunocompromised subjects, *Corynebacterium pseudotuberculosis* that causes abscesses, i.a. in the lungs, in sheep, goats, horses and occasionally also in humans, etc. All of these bacterial species have in common the ability to survive within macrophages, infect them and replicate within this type of host cell.

This typical property seriously hampers the treatment for disorders (in this specification the term "disorder" is used as an equivalent for "disease") arising from an infection with a bacterium that belongs to the group of macrophage surviving nocardioform actinomycetes. In many cases, treatment is with antibiotics when clinical signs are actually present. This however is cumbersome since a significant amount of the bacteria are present within macrophages and hard to reach by antibiotics. Treatment with antibiotics therefore often takes a long treatment time, and with mixed success. For diseases such as tuberculosis in humans, nocardiosis in fish and pneumonia in foals, prophylactic treatment would be preferred. Such prophylactic treatment typically relies on the use of a vaccine comprising killed or live attenuated bacteria derived from wild type bacteria. With regard to the macrophage surviving nocardioform actinomycetes, killed vaccines (i.e vaccines comprising killed bacteria or one or more subunits thereof as the therapeutic agent) have proven to be unsuccessful. At present it is generally believed that one needs live bacteria for a successful prophylactic treatment against macrophage surviving nocardioform actinomycetes, since only these can have the capability of reaching the macrophages and mimic wild-type bacteria sufficiently to trigger an adequate immune response. Indeed, to treat tuberculosis, a live vaccine (BCG, Bacille Calmette Guérin) is available based on the species *Mycobacterium bovis* which species is very closely related to the species *Mycobacterium tuberculosis*. However, the protective effect is not impressive. With regard to Nocardiaceae species such as *Rhodococcus equi* and *Nocarida seriolae*, no vaccines are currently commercially available. With regard to the species *Corynebacterium pseudotuberculosis* control has been attempted using autogenous vaccines, however with mixed success (RUMA Guidelines, National Office of Animal health, Hertfordshire, United Kingdom, 2006).

There is clearly a need for adequate prophylactic treatment to protect an animal against a disorder arising from an infection with macrophage surviving nocardioform actinomycetes. Treatment in this sense means stimulating the immune system of the target animal sufficiently to at least reduce the negative effects of a challenge with wild-type micro-organisms. The goal is that this leads to a protection against the disorder, i.e. the disorder is prevented, or at least the level of infection or the clinical signs of disease in the animal are diminished, and consequently the severity of disease is diminished as well. The fact that the macrophage surviving nocardioform actinomycetes have adopted the same strategy for surviving in a host brings about the idea of a common strategy for prophylactic treatment against an infection with these bacteria.

In this respect it is noted that it has been described in literature that cholesterol metabolism plays a crucial role in the survival of nocardioform actinomycetes in macrophages and might be an important virulence factor (Proceedings of the National Academy of Science, Feb. 6, 2007, vol. 104, no. 6, pp 1947-1952). It was also suggested that this metabolism provides logical targets for novel therapeutic agents to combat disease causing strains, i.e. drugs for treatment after infection has occurred. Indeed, when applying hindsight there is other supporting evidence for the established fact that for all macrophage surviving nocardioform actinomycetes, cholesterol metabolism plays a role in the survival and persistence of the bacteria in host macrophages. For example, from chapter 11 (titled: *Rhodococus equi*: Pathogenesis and Replication in Macrophages) in "Opportunistic Intracellular Bacteria and Immunity", by Lois J. Paradise et al (eds.), New York, 1999) it is known that there are great similarities in the clinical symptomatology between infections caused by several nocardioform actinomycetes and cholesterol oxidase was determined to be an enzymatic component of virulence factors. In Veterinairy Microbiology, Volume 56, Issue 3-4, June 1997, 269-276 it is shown that *Corynebacterium pseudotuberculosis* is involved in the cholesterol oxidase process together with *Rhodococcus equi*.

Therefore, at first glance it seems tempting to develop a pharmaceutical composition to protect an animal against a disorder arising from an infection with macrophage surviving nocardioform actinomycetes (such a composition can also be referred to as a vaccine), using the recognition that cholesterol metabolism plays a crucial role in the survival of these bacteria in the macrophages. However, once realising that the suggestions made in the PNAS article referred to here-above (2007 article) related to a drug, and thus aimed at completely killing the bacteria by interfering in their cholesterol metabolism, pursuing that same strategy seems to be unsuitable for a live vaccine: if one tries to attenuate a bacterium by cutting of it's survival at the essential site of replication, the bacterium will not replicate and persist in the host animal. Indeed, for a treatment with drugs this is an ideal situation. However, for a live vaccine, if one completely blocks survival of the bacterium, one expects to mimic a vaccine comprising killed bacteria.

Such vaccines have proven to be unsuccessful for treating macrophage surviving nocardioform actinomycetes. Still, attempts have been performed to assess the use of live bacteria that are crippled in their cholesterol metabolism, in a pharmaceutical composition for protecting an animal against a challenge with wild type disease causing nocardioform actinomycetes. An example of such attempts is a live vaccine based on a cholesterol oxidase (ChoE) mutant of wild type *Rhodococcus equi* strain 103+ (Prescott in Veterinary Microbiology 118, 2006, pp 240-246). This attempt was unsuccessful. However, not because it induced no protection, as one would expect based on the technical teachings of the PNAS article as referred to here-above (PNAS Feb. 6, 2007, vol. 104, no. 6, pp 1947-1952), but because the mutant strain was still too virulent. The mutant could still survive and multiply in macrophages at a level comparable to wild-type *R. equi*. Also, the antigenic load of this cholesterol cripple mutant appeared to be comparable with that of a wild-type organism. Therefore, the mutant was still capable of inducing disease. Indeed, in the mean time it has also been established that a live mutant *Rhodococcus equi* that is unable to take up cholesterol at all (sterol uptake permease mutant supAB as presented by Van der Geize et al. at the 4th Havemeyer Workshop on *Rhodococcus equi*, Edinburgh, 13-16 Jul., 2008; and Van der Geize et al.: "A novel method to generate unmarked gene deletions in the intracellular pathogen *Rhodococcus equi* using 5-fluorocytosine conditional lethality" in Nucleic Acids Research 2008; doi: 10.1093/nar/gkn811, further on also referred to as "Van der Geize et al., 2008"), which means that the complete cholesterol metabolism is blocked (at least when cholesterol is used as the starting compound), is still capable of surviving and persisting in macrophages (Van der Geize et al., 2008) and thus is still too virulent. In order to attenuate a live *Rhodococcus equi* one appears to need an additional mutation having an effect outside the cholesterol metabolism (Prescott: Veterinary Microbiology 125, 2007, 100-110). Based on these results, it was concluded that cholesterol metabolism as such is not an important virulence factor and cannot be used to sufficiently attenuate these bacteria. Bacteria having mutations in their cholesterol metabolism apparently have the same, or at least a comparable antigenic load as the wild type organism and thus, although capable of providing adequate protection (that is: if the subject animal survives the challenge with the mutated bacteria), are far too virulent to be used in a pharmaceutical composition. Thus, targeting at a pharmaceutical composition for prophylactic treatment, which composition contains live bacteria that are attenuated by inactivating genes involved in the cholesterol metabolism, is thought to be a dead end street.

Surprisingly however applicant found that in order to protect an animal against a disorder arising from an infection with a macrophage surviving nocardioform actinomycete, one can use a pharmaceutical composition comprising live bacteria of a nocardioform actinomycetes species (typically being of the same species as the infecting bacterium or alternatively, being of a very closely related species, thus having many T-cell epitopes in common such as is the case with *Mycobacterium tuberculosis* vs *Mycobacterium bovis*), the live bacteria are attenuated by inactivation of a gene that encodes a protein involved in methylhexahydroindanedione propionate degradation, and a pharmaceutically acceptable carrier for carrying the bacteria.

"Attenuated" in this sense means being incapable of inducing a full suite of symptoms of the disease that is normally associated with the virulent (often wild-type) pathogenic counterpart of the attenuated bacterium.

"Inactivation" in the sense of the present invention means that a gene, for example while being part of an operon (i.e. the set of genes necessary to actually express the protein at a functional level) is either removed completely from the genome or changed (by any known, or even yet to be devised technique; see e.g. Introduction to Biotechnology and Genetic Engineering, A. J. Nair, INFINITY SCIENCE PRESS LLC, 2008, chapter 13 "Genetic Techniques", pp 476-496 and chapter 15 "Recombinant DNA Technology", pp 563-612) such that it no longer encodes the corresponding wild-type protein, or is no longer accessible for complete transcription, or any other change in the genome such that the wild-type protein will not be made by the attenuated bacterium in vivo, at least not at level suitable to support normal methylhexahydroindanedione propionate catabolism when compared to a situation wherein the gene (or operon, if applicable) is in a form suitable to support normal metabolism.

"Encoding a protein" in the sense of the present invention means that the gene (for example while being part of an operon) directly encodes the protein or a subunit of the protein (multiplesubunits together forming the enzymatically active protein), or encodes one or more intermediates that are converted, either directly or via multiple steps, in the protein or subunit thereof (multiple subunits together forming the enzymatically active protein).

A "pharmaceutically acceptable carrier" can be any solvent, dispersion medium, coating, antibacterial and antifungal agent, isotonic and absorption delaying agent, and the like that are physiologically compatible with and acceptable for the target animal, e.g. by being made i.a. sterile. Some examples of such carrying media are water, saline, phosphate buffered saline, bacterium culture fluid, dextrose, glycerol, ethanol and the like, as well as combinations thereof. They may provide for a liquid, semi-solid and solid dosage form, depending on the intended mode of administration. As is commonly known, the presence of a carrying medium is not essential to the efficacy of a vaccine, but it may significantly simplify dosage and administration of the antigen. Next to the carrier and antigen, the pharmaceutical composition may comprise other substances such as adjuvants, stabilisers, viscosity modifiers or other components are added depending on the intended use or required properties of the composition.

Figure 3:
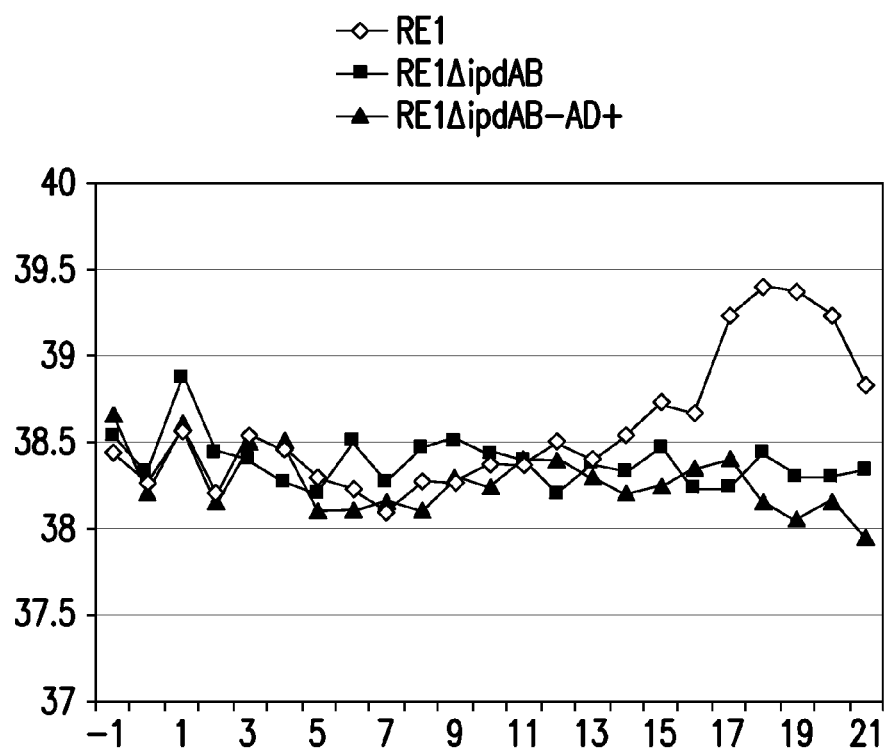
FIG. 3: Rectal temperature post-challenge.

In the pharmaceutical composition of the present invention, live bacteria are present, which bacteria are mutated such that a gene that encodes a protein involved in methylhexahydroindanedione propionate degradation is inactivated. As is commonly known, methylhexahydroindanedione propionate (also known as HIP or 3α-H-4α(3'-propionic acid)-7aβ-methylhexahydro-1,5-indanedione) and 5-hydroxy-methylhexahydroindanone propionate (also known as HIL or 3aα-H-4α(3'-propionic acid)-5α-hydroxy-7aβ-methylhexahydro-1-indanone-δ-lactone) are formed during the degradation of cholesterol by actinobacteria, including the macrophage surviving nocardioform actinomycetes. Recently, an operon (called ipdAB: indanedione proprionate degradiation Alfa+Beta) has been identified in bacterial species that belong to the suborder of Corynebacterineae that encodes the a and R subunit of a transferase that is involved in HIP degradation (see co-pending International Patent application PCT/EP2008/060844, filed 19 Aug. 2008, based on a US priority application filed 21 Aug. 2007). The known transferase knock out mutant is no longer capable of degrading HIP and HIL (see FIG. 3 of the patent application referred to here-above) nor does it grow on HIP, HIL or 4-androstene-3, 17-dione. In any case, "involved in HIP degradation" means that a knock out mutant is no longer capable of growth on HIP as a sole carbon and energy source, or at least not capable of growth on HIP at a level obtainable by a non-mutant bacterium. At present it is not clear whether the transferase catabolises HIP degradation itself or whether a reaction is catalysed on which HIP degradation depends. Still, HIP degradation occurs at a relatively late stage in the cholesterol metabolism and is a very specific step in the cholesterol degradation pathway. Based on the publicly available knowledge about mutations in the cholesterol metabolism (Prescott references mentioned here-above), one would expect that this mutation would lead to a live bacterium that, although providing a protective effect, would be far too virulent. To applicant's surprise however, such a mutant appears to be adequately attenuated which is due to significantly reduced survival capabilities of the mutant within macrophages. The reason why a gene that is involved in HIP degradation plays such an important role in survival within macrophages is unclear. It even seems to contradict prior art results which show that even a complete blockade of cholesterol metabolism has a poor attenuating effect, apparently since there is no effect on the macrophage survival capabilities of the nocardioform actinomycetes. Therefore, it was quite surprising to find that the present mutation, which affects a minor step along the pathway of cholesterol catabolism, severely hampers the survival capabilities of pathogenic nocardioform actinomycetes in macrophages. In particular, it has been found that the mutant live bacteria are still able to enter the macrophages and persist in them (hence securing the stimulus of a protective immune response), but at a very low level, which appears to significantly reduce their virulence, which on its turn makes them acceptable for prophylactic treatment.

In an embodiment, multiple genes in one operon are inactivated. By inactivating multiple genes the chances of a change of the bacterium to a wild-type (resembling) phenotype will decrease. In particular, the genes ipdA and ipdB are inactivated. By inactivating these genes, an effective and safe attenuation can be provided for. In a preferred embodiment the inactivation is realised by deleting at least one gene by unmarked gene deletion. An advantage of unmarked mutation is that it allows the repetitive introduction of mutations in the same strain. Foreign DNA (vector DNA) is removed in the process of introducing the mutation. Newly introduced vector DNA, for the introduction of a second mutation, therefore cannot integrate at the site of the previous mutation (by homologous recombination between vector DNA's). Integration will definitely happen if vector DNA is still present in the chromosome and will give rise to a large number of false-positive integrants. The system enables the use of a sole antibiotic gene for the introduction of an infinite number of mutations. Unmarked mutation also allows easy use in the industry because of the absence of heterogeneous DNA allowing easy disposal of fermentation broth. Gene inactivation by gene deletion enables the construction of stable, non-reverting mutants. Especially small genes (<500 bp) are inactivated more easily by gene deletion compared to gene disruption by a single recombination integration. Gene deletion mutagenesis can also be applied to inactivate a cluster of several genes from the genome. The gene deletion mutagenesis strategy can be applied also for gene-replacement (e.g. changing wild type into mutant gene).

In an embodiment the bacteria belong to the family of Nocardiaceae or Mycobacteriaceae. Preferably, the bacteria belong to the genera *Rhodococcus, Nocardia* or *Mycobacterium* and in particular belong to any of the species *Rhodococcus equi, Nocardia seriolae, Mycobacterium tubercolosis, Mycobacterium ulcerans, Mycobacterium bovis* or *Mycobacterium avium* paratubercolosis. With regard to these species, adequate vaccines are not commercially available to date. The present invention allows the provision of pharmaceutical compositions that can be used as vaccines to combat these bacteria and therefore mitigate the corresponding diseases they cause in an animal.

In an embodiment the pharmaceutical composition is in a form suitable for oral administration. Besides the fact that it is a very convenient way of administration, it has in particular become clear that this way of administration is safe. Parenteral administration may give rise to abscesses. Preferably the live bacteria are present in a concentration between $1 \times 10^4$ and $1 \times 10^{10}$ CFU per dose.

The present invention also pertains to *Rhodococcus equi* bacteria derived from a strain as deposited under the Budapest Treaty with the Collection Nationale de Cultures de Microorganismes of the Institut Pasteur at 25, du Docteur Roux, F-75724 Paris France under nr. CNCM I-4108 or nr. CNCM I-4109 on Jan. 6, 2009 and to bacteria that belong to this strain. The Applicants agree that during the pendency of this application, access to the deposits will be afforded to the Commissioner upon request and that subject to 37 C.F.R. §1.808 (2)(b) all restrictions regarding public access to the de deposited material will be irrevocably removed upon the grant of a patent on this application.

The present invention also pertains to the use of live bacteria that belong to the group of nocardioform actinomycetes having the ability to survive within macrophages of an animal, the live bacteria being attenuated by inactivation of a gene that encodes a protein involved in methylhexahydroindanedione propionate degradation, to manufacture a pharmaceutical composition to protect an animal against a disorder arising form an infection with a corresponding wild-type bacterium.

The invention also pertains to a method of treating an animal to protect it against a disorder arising from an infection with a bacterium that belongs to the group of nocardioform actinomycetes having the ability to survive within macrophages of an animal, comprising administering to the animal a pharmaceutical composition comprising live bacteria of a nocardioform actinomycetes species, which live bacteria are attenuated by inactivation of a gene that encodes a protein involved in methylhexahydroindanedione propionate degradation.

The invention will be further explained using the following examples describing specific embodiments of the present invention, which embodiments are spread over three parts:
Part A: Identification and construction of strains
Part B: Macrophage survival as a model for in vivo attenuation
Part C: Efficacy of mutant bacteria in protection against infection with wild-type
Part A: Identification and Construction of Strains
A1 Culture Media and Growth Conditions

*R. equi* strains were grown at 30° C. (200 rpm) in Luria-Bertani (LB) medium consisting of Bacto-Tryptone (BD), Yeast Extract (BD) and 1% NaCl (Merck) or mineral acetate medium. *M. smegmatis* mc²155 (Snapper et al., 1990, *Mol. Microbiol.* 4:1911-1919) was grown at 37° C. (200 rpm) in BBL trypticase soy broth (TSB; BD) supplemented with 0.05% Tween80. Mineral acetate medium (MM-Ac) contained $K_2HPO_4$ (4.65 g/l), $NaH_2PO_4.H_2O$ (1.5 g/l), Na-acetate (2 g/l), $NH_4Cl$ (3 g/l), $MgSO_4.7H_2O$ (1 g/l), thiamine (40 mg/l, filter sterile; Sigma), and Vishniac stock solution (1 ml/l). Vishniac stock solution was prepared as follows (modified from Vishniac and Santer, 1957, *Rev.* 21: 195-213): EDTA (10 g/l) and $ZnSO_4.7H_2O$ (4.4 g/l) were dissolved in distilled water (pH 8 using 2 M KOH). Then, $CaCl_2.2H_2O$ (1.47 g/l), $MnCl_2.7H_2O$ (1 g/l), $FeSO_4.7H_2O$ (1 g/l), $(NH_4)_6Mo_7O_{24}.4H_2O$ (0.22 g/l), $CuSO_4.5H_2O$ (0.315 g/l) and $CoCl_2.6H_2O$ (0.32 g/l) were added in that order at pH 6 and finally stored at pH 4.

For growth on solid media Bacto-agar (15 g/l; BD) was added. 5-Fluorocytosine (Sigma-Aldrich) stock solution (10 mg/ml) was prepared in distilled water, dissolved by heating to 50° C., filter-sterilized and added to autoclaved media.

*Nocardia seriola* strain INS436 was routinely grown at 26° C. (200 rpm) in Eugon Broth (BD) supplemented with Tween80 (0.05%). For growth on solid media Bacto-agar (15 g/l; BD) was added. Sucrose (2%) was added to the agar medium for sacB dependent sucrose selection.
A2 Identification of ipdA, ipdB and fadE30 in *R. equi* Strain 103+, and ipdAB in *N. seriolae* INS436

As indicated here-above, the ipdA and ipdB genes of *Rhodococcus* are found to be involved in the degradation of methylhexahydroindanedione propionate (HIP; 3aα-H-4α (3'-propionic acid)-7aβ-methylhexahydro-1,5-indanedione) and 5-hydroxy-methylhexahydroindanone propionate (HIL; 3aα-H-4α(3'-propionic acid)-5α-hydroxy-7aβ-methylhexahydro-1-indanone-δ-lactone). Bioinformatics analyses of the protein sequences of IpdA and IpdB of *R. erythropolis* strain SQ1 in genome databases revealed that the genes encoding IpdA and IpdB and their apparent operonic organization were conserved in the genome of *R. equi* 103+ (wild-type strain obtained from J. F. Prescott, Ontario, Canada; as referred to in Veterinary Microbiology 118 (2006) 240-246). The *R. equi* 103+ genome sequence has been determined by the *R. equi* sequencing group at the Sanger Institute, Hinxton, Cambridge, UK (genome published as "*R. equi* 103S"). Genome analysis furthermore revealed that *R. equi* 103+ harbors additional paralogous genes of ipdA and ipdB, designated ipdA2 and ipdB2, respectively. These genes are located outside the cholesterol catabolic gene cluster. The amino acid sequences of IpdA, IpdB, IpdA2 and IpdB2 are depicted in the appended SEQ ID's under No 1, 2, 3 and 4 respectively. Amino acid sequence identities of the IpdA and IpdB proteins of *R. equi* 103+ with these paralogues and several other actinobacterial orthologues are listed in Table 6. This table gives an overview of genes identified in other genomes of nocardioform actinomycetes, encoding orthologues of IpdA and IpdB of *Rhodococcus equi* 103+. In connection with the present invention, these and other orthologues are called IpdA and IpdB. Protein identity indicates percentage full length amino acid sequence identity with IpdA and IpdB of *R. equi* 103S. Actinobacterial genome sequences were obtained from the genomic BLAST server for microbial genomes of the National Center for Biotechnology Information (NCBI). The *R. equi* 103+ sequence data were produced by the *R. equi* Sequencing Group at the Sanger Institute. The genome of strain 103+ (known as 103S) was used for these identification purposes. Practical work with *Rhodococcus equi*, as exemplified hereafter, was carried out with *R. equi* strain RE1 (isolated from a foal suffering from granulomatous pneumonia caused by *Rhodococcus equi* infection).

TABLE 6

Overview of genes

| Actinobacterial strain | IpdA Gene ID | Protein Identity (%) | IpdB Gene ID | Protein Identity (%) |
|---|---|---|---|---|
| Rhodococcus equi 103S | ipdA | 100 | ipdB | 100 |
| Rhodococcus equi 103S | ipdA2 | 55 | ipdB2 | 51 |
| Rhodococcus jostii RHA1 | Ro04651 | 79 | Ro04650 | 77 |
| Rhodococcus erythropolis SQ1 | ipdA | 76 | ipdB | 74 |
| Mycobacterium tuberculosis H37Rv | Rv3551 | 69 | Rv3552 | 67 |
| Mycobacterium bovis AF2122/97 | Mb3581 | 69 | Mb3582 | 67 |
| Mycobacterium avium subsp. paratuberculosis K-10 | MAP0515c | 72 | MAP0514c | 68 |
| Mycobacterium avium 104 | MAV_0609 | 72 | MAV_0608 | 68 |
| Mycobacterium ulcerans Agy99 | MUL_4114 | 67 | MUL_4115 | 66 |
| Mycobacterium marinum M | MMAR_5040 | 69 | MMAR_5041 | 65 |
| Mycobacterium vanbaalenii PYR-1 | Mvan_5267 | 71 | Mvan_5268 | 67 |
| Mycobacterium gilvum PYR-GCK | Mflv_1489 | 72 | Mflv_1488 | 68 |
| Mycobacterium sp. MCS | Mmcs_4684 | 71 | Mmcs_4685 | 70 |
| Mycobacterium sp. JLS | Mjls_5069 | 71 | Mjls_5070 | 70 |
| Mycobacterium smegmatis MC2 155 | MSMEG_6002 | 72 | MSMEG_6003 | 69 |
| Mycobacterium abscessus | MAB_0605c | 73 | MAB_0604c | 74 |
| Nocardia farcinica IFM 10152 | Nfa5090 | 71 | Nfa5080 | 72 |

A second gene involved in the degradation of methylhexahydroindanedione propionate is fadE30. The ΔfadE30 mutant is severely impaired in growth on HIL and HIP, showing virtually no growth after 24 hours of incubation. The fadE30 gene of Rhodococcus equi was identified by a protein sequence similarity search performed on the R. equi 103+ genome available at the Sanger Institute (http://www.sangser.ac.uk). The annotated protein sequence of FadE30 of Rhodococcus jostii strain RHA1 (Ro4596, Genbank accession number ABG96382) was used as a protein sequence template (McLeod et al., 2006, in Proc. Natl. Acad. Sci. U.S.A. 103:15582-15587; and Van der Geize et al., 2007, in Proc. Natl. Acad. Sci. U.S.A. 104:1947-1952). A database similarity search with Ro4596 revealed a gene of R. equi 103S, encoding a protein that displayed 73% amino acid sequence identity to Ro4596. This protein was annotated as FadE30 of R. equi 103S (SEQ ID No 43) and its corresponding gene was termed fadE30. Orthologous genes, encoding FadE30 in other actinobacteria, could be identified in a similar way. A selection of these is listed in Table 8.

TABLE 8

Overview of genes

| Actinobacterial strain | FadE30 Gene ID | Protein Identity (%) |
|---|---|---|
| Rhodococcus equi 103S | fadE30 | 100 |
| Rhodococcus opacus B4 | ROP_45410 | 74 |
| Rhodococcus jostii RHA1 | Ro04596 | 75 |
| Rhodococcus erythropolis PR4 | RER_08910 | 72 |
| Mycobacterium tuberculosis H37Rv | Rv3560c | 68 |
| Mycobacterium bovis AF2122/97 | Mb3590c | 68 |
| Mycobacterium avium subsp. paratuberculosis K-10 | MAP0507 | 69 |
| Mycobacterium ulcerans Agy99 | MUL_4125 | 69 |
| Mycobacterium marinum M | MMAR_5049 | 69 |
| Mycobacterium vanbaalenii PYR-1 | Mvan_5285 | 69 |
| Mycobacterium gilvum PYR-GCK | Mflv_1481 | 69 |
| Mycobacterium sp. MCS | Mmcs_4693 | 68 |
| Mycobacterium smegmatis MC2 155 | MSMEG_6012 | 66 |
| Mycobacterium abscessus | MAB_0597 | 71 |
| Nocardia farcinica IFM 10152 | Nfa4840 | 76 |
| Salinispora tropica CNB-440 | Strop_2615 | 64 |
| Salinispora arenicola CNS-205 | Sare_2814 | 65 |
| Streptomyces avermitilis MA-4680 | SAV_3834 | 59 |
| Nocardioides sp. JS614 | Noca_2767 | 65 |

The ipdAB genomic locus of N. seriola was amplified by PCR in three parts, using oligonucleotide primers developed on highly conserved nucleotide sequences of the actinobacterial ipdAB locus. These conserved regions were identified by nucleotide sequence alignment of several known actinobacterial sequences of the ipdAB genes. The nucleotide genome sequence of the ipdAB region of Nocardia farcinica (nfa05080-nfa05090) (DDBJ accession number AP006618) was used as a primary template to develop the oligonucleotide PCR primers. The primer oligonucleotide sequences used are listed in Table 5. Chromosomal DNA of N. seriola INS436 was used as template for PCR. The ipdAB genes of N. seriola were amplified using primers ipdA-actino-F and ipdB-actino-R(PCR 22), the upstream region of ipdAB was amplified using ipd-actino-F2 and ipdA-actino-R(PCR 23), and the downstream region was amplified using ipdB-actino-F and ipd-actino-R(PCR 21). PCR products were cloned into the pGEM-T cloning vector and the nucleotide sequences of the inserts were determined. Different primer pairs were subsequently developed on the obtained DNA sequence and used to re-clone and re-sequence the ipd locus. This resulted in a complete nucleotide sequence of the ipdAB locus of N. seriola covering 4,139 bp. The sequenced DNA fragment contained the ipdA and ipdB genes of N. seriola and their neighboring genes. The deduced protein sequences of IpdA and IpdB of N. seriola INS436 are shown in SEQ ID NO 58 and SEQ ID NO 59 respectively.

A3 Cloning, PCR and Genomic DNA Isolation

Escherichia coli DH5α was used as host for all cloning procedures. Restriction enzymes were obtained from Fermentas GmbH. Chromosomal DNA of cell cultures was isolated using the GenElute Bacterial Genomic DNA Kit (Sigma-Aldrich) according to the instructions of the manufacturer.

PCR was performed in a reaction mixture (25 µl) consisting of Tris-HCl (10 mM, pH 8), 1× standard polymerase buffer, dNTPs (0.2 mM), DMSO (2%), PCR primers (10 ng/µl each, Table 5) and High-Fidelity DNA polymerase enzyme (Fermentas) or Pwo DNA polymerase (Roche Applied Science). For colony PCR, cell material was mixed with 100 µl of chloroform and 100 µl of 10 mM Tris-HCl pH 8, vortexed vigorously and centrifuged (2 min, 14,000×g). A sample of the upper water phase (1 µl) was subsequently used as template for PCR. A standard PCR included a 5 min 95° C. DNA melting step, followed by 30 cycles of 45 sec denaturing at 95° C., 45 sec annealing at 60° C. and 1-3 min elongation at 72° C. The elongation time used depended on the length of the expected PCR amplicon, taking 1.5 min/1 kb as a general rule.

TABLE 5

Oligonucleotides used for PCR.

| PCR | PCR Amplicon | Size (bp) | Oligonucleotide sequence | (SEQ ID NO) |
|---|---|---|---|---|
| 1 | Upstream region R. equi RE1 ipdAB (construction pSelAct-ipd1) | 1,368 | ipdABequiUP-F TGCCGCTGACGGAGGAGATCAT<br>ipdABequiUP-R GATATCATACCGGCGACTGCCTCATCCA | (5)<br>(6) |
| 2 | Downstream region R. equi RE1 ipdAB (construction pSelAct-ipd1) | 1,396 | ipdABequiDOWN-F GATATCGAACCACCCGTGGTCACCAAC<br>ipdABequiDOWN-R TCGAGCAGCGAACTGGCCTGAA | (7)<br>(8) |
| 3 | Upstream region R. equi RE1 ipdAB (confirmation ΔipdAB mutant) | 1,726<br>(wt: 3,067) | ipdABequiContrUP-F AGTCCGACGACGATCGAGTTGA<br>ipdABequiContr-R TCACGCCGAGACCTCACGGTCA | (9)<br>(10) |
| 4 | Downstream region R. equi RE1 ipdAB (confirmation ΔipdAB mutant) | 1,682<br>(wt: 3,023) | ipdABequiContr-F ATGGCTGAGAAGCGCGACAAGC<br>ipdABequiContrDOWN-R TCGTCGTCGTCTCGCACCAGAT | (11)<br>(12) |
| 5 | ipdAB operon R. equi RE1 (confirmation ΔipdAB mutant) | 296<br>(wt: 1,636) | ipdABequiContr-F2 ATGGCTGAGAAGCGCGACAAGC<br>ipdABequiContr-R2 TCACGCCGAGACCTCACGGTCA | (13)<br>(14) |
| 6 | Upstream region R. equi RE1 ipdAB2 (construction pSelAct-ΔipdAB2) | 1,444 | ipdAB2equiUP-F TCGAGGTGGTTCATGACGAAGA<br>ipdAB2equiUP-R AGATCTCCGGCCGACCACCTCTTTCTCC | (15)<br>(16) |
| 7 | Downstream region R. equi RE1 ipdAB2 (construction pSelAct-ΔipdAB2) | 1,387 | ipdAB2equiDOWN-F AGATCTAGTGCGGAGGAGCTGGAACTGA<br>ipdAB2equiDOWN-R ACTAGTGATCTCGTCCGTGACCTGATG | (17)<br>(18) |
| 8 | Upstream region R. equi RE1 ipdAB2 (confirmation ΔipdAB2 mutant) | 1,557<br>(wt: 3,053) | ipdAB2ContUP-F CCGACATCACGGTGTCGGGATC<br>ipdAB2Contr-R TCACGCGGGAACCTCCTTGTCG | (19)<br>(20) |
| 9 | Downstream region R. equi RE1 ipdAB2 (confirmation ΔipdAB2 mutant) | 1,471<br>(wt: 2,967) | ipdAB2Contr-F TTGTCGGACAAGAGAATGTCGG<br>ipdAB2ContDOWN-R GGTCGTGACGTCCGCGGTGTTC | (21)<br>(22) |
| 10 | ipdAB2 operon R. equi RE1 (confirmation ΔipdAB2 mutant) | 123<br>(wt: 1,619) | ipdAB2contr-F TTGTCGGACAAGAGAATGTCGG<br>ipdAB2contr-R TCACGCGGGAACCTCCTTGTCG | (23)<br>(24) |
| 11 | vapA R. equi RE1 | 408 | vapA-F GCAGCAGTGCGATTCTCAATAG<br>vapA-R TAACTCCACCGGACTGGATATG | (25)<br>(26) |
| 12 | Upstream region ipdAB genes M. smegmatis mc²155 (construction pK18-ipdABsmeg) | 1,502 | ipdABsmegUP-F TTCGAGATGGCCGCGATCGAAT<br>ipdABsmegUP-R ACTAGTGATGGTCATGCCGCTCTCGATA | (27)<br>(28) |
| 13 | Downstream region ipdAB genes M. smegmatis mc²155 (construction pK18-ipdABsmeg) | 1,431 | ipdABsmegDOWN-F ACTAGTCAGGTCGCCGACAACACCTCGT<br>ipdABsmegDOWN-R AAGCTTGAATTCGTCGCCGACGGTGAAG | (29)<br>(30) |
| 14 | ipdAB operon M. smegmatis mc²155 (confirmation ΔipdAB mutant) | 273<br>(wt: 1,697) | ipdABMsmegcont-F ACGCCAGCTACCGCATGGAA<br>ipdABMsmegcont-R ATCACCTCGCGCAGCAGCTT | (31)<br>(32) |
| 15 | Upstream region R. equi RE1 fadE30 (construction pSelAct-fadE30) | 1,511 | fadE30equiUP-F TCCATTCGCGCCAGCGCATTCT<br>fadE30equiUP-R AGATCTCTTCGAGCCATTCGCGAAT | (33)<br>(34) |
| 16 | Downstream region R. equi RE1 fadE30 (construction pSelAct-fadE30) | 1,449 | fadE30equiDOWN-F AGATCTACGGCGGATCCAACGAGAT<br>fadE30equiDOWN-R AGGTCGCGGAACTCCTGGTTAC | (35)<br>(36) |
| 17 | Upstream region R. equi RE1 fadE30 (confirmation fadE30 mutant) | 1,866<br>(wt: 2,909) | fadE30UPcontr-F ACGATGTACGCACGACCGACCT<br>fadE30contr-R GACAGCTTCTCGACGGTCTCAC | (37)<br>(38) |
| 18 | Downstream region R. equi RE1 fadE30 (confirmation fadE30 mutant) | 1,767<br>(wt: 2,811) | fadE30contr-F AGGCGAGGCGGAACCTCTATAC<br>fadE30DOWNcontr-R CGTCCAGAACGATGGAGAGGTA | (39)<br>(40) |
| 19 | fadE30 locus R. equi RE1 (confirmation fadE30 mutant) | 428<br>(wt: 1,470) | fadE30cont-F AGGCGAGGCGGAACCTCTATAC<br>fadE30cont-R GACAGCTTCTCGACGGTCTCAC | (41)<br>(42) |
| 20 | Upstream region of ipdAB of N. seriola INS436 for sequence determination ipd locus | 1,644 | ipd-actino-F2 GGTGGTCGTTCGCCGCCGCCGTG<br>ipdA-actino-R CGATGCCGATGGTCATGCCGCT | (44)<br>(45) |
| 21 | Downstream region of ipdAB of N. seriola INS436 for sequence determination ipd locus | 1,381 | ipdB-actino-F GGCAACCAGAACCTCTCCGCCTTCGG<br>ipd-actino-R GTGTTGCCCTCGACCAGGCCGGCGCAACAGCAT | (46)<br>(47) |
| 22 | Part of ipdAB genes of N. seriola INS436 for sequence determination ipd locus | 1,162 | ipdA-actino-F AGCGGCATGACCATCGGCATCG<br>ipdB-actino-R CCGAAGGCGGAGAGGTTCTGGTTGCC | (48)<br>(49) |
| 23 | ipdAB genes of N. seriola INS436 for sequence determination ipd locus and to confirm ipdAB gene deletion | 222<br>(wt: 1,634) | ipdABNser-F ATGCGCGACAAGCGAATGAGCCT<br>ipdABNser-R TCATGCCGTCACTTCCTTCCCG | (50)<br>(51) |
| 24 | Upstream region of ipdAB for construction of plasmid for ipdAB gene deletion | 1,487 | ipdABNserUP-F TCCTCGTCGCCGTAGTGCAGGT<br>ipdABNserUP-R CCCGGGATGGTCATGCCGCTGCGGAGC | (52)<br>(53) |
| 25 | Downstream region of ipdAB for construction of plasmid for ipdAB gene deletion | 1,049 | ipdABNserDOWN-F CCCGGGTGTGTCCGCCGACGAG<br>ipdABNserDOWN-R TTGGCGGCCCATGATGACCTGGG | (54)<br>(55) |
| 26 | Downstream region of ipdAB to confirm ipdAB gene deletion | 1,148<br>(wt: 2,560) | ipdABNser-F2 ATGCGCGACAAGCGAATGAGCCT<br>ipdABNserDOWN-Contr-R GCCTTCCACCAGACCGGCTTTG | (56)<br>(57) |

A4 Electrotransformation of R. equi, M. smegmatis and N. seriolae

Cells of R. equi strains were transformed by electroporation essentially as described (Van der Geize et al., in the accepted NAR paper referred to here-above; Navas et al., 2001, J. Bacteriol. 183: 4796-4805). Briefly, cell cultures were grown in 50 ml LB at 30° C. until $OD_{600}$ reached 0.8-1.0. The cells were pelleted (20 min at 4,500×g) and washed twice with 10% ice-cold glycerol. Pelleted cells were re-suspended in 0.5-1 ml ice-cold 10% glycerol and divided into 200 µl aliquots.

Cells of M. smegmatis mc²155 were transformed by electroporation essentially as described (Jacobs et al., 1991, Methods Enzymol. 204:537-555). Briefly, cell cultures (250 ml) were grown at 37° C. in TSB medium+0.05% Tween80 until $OD_{600}$ reached 0.8, put on ice for one and a half hour and centrifuged (10 min at 5,000×g) to pellet the cells. Cell pellets were washed twice with distilled water and resuspended in a final volume of 1 ml 10% glycerol and divided into 200 µl aliquots.

MilliQ-eluted plasmid DNA (5-10 µl; GenElute Plasmid Miniprep Kit, Sigma-Aldrich) was added to 200 µl cells in 2 mm gapped cuvettes. Electroporation was performed with a single pulse of 12.5 kV/cm, 1000Ω and 25 µF. Electroporated cells were gently mixed with 1 ml LB medium (*R. equi*) or 1 ml TSB+0.05% Tween80 (*M. smegmatis*) and allowed to recover for 2 h (*R. equi*) or 5 h (*M. smegmatis*) at 37° C. and 200 rpm. Aliquots (200 µl) of the recovered cells were plated onto selective agar medium. *R. equi* transformants were selected on LB agar containing apramycin (50 µg/ml) and appeared after 2-3 days of incubation at 30° C. *M. smegmatis* transformants were selected on TSB+0.05% Tween80 agar containing kanamycin (10 µg/ml) and appeared after 4-5 days of incubation at 37° C.

For *N. seriolae*, a pre-culture (20 ml) of strain INS436 was grown for 5 days at 26° C. (200 rpm) in Eugon broth+0.05% Tween80 ($OD_{600nm}$=6) and used to inoculate 100 ml of fresh Eugon broth+0.05% Tween80 medium (1:100). The primary culture was grown overnight at 26° C. for 20 hours to $OD_{600nm}$=1.3.

The cells were pelleted (20 min, 4000 g) at 4° C. and washed twice with 50 ml ice-cold 10% glycerol. The pelleted cells were resuspended in 500 µl 10% glycerol, divided into 200 µl aliquots and immediately used for electrotransformation. MilliQ-eluted plasmid DNA (5-10 µl; GenElute Plasmid Miniprep Kit, Sigma-Aldrich) was added to 200 µl cells in a 2 mm gapped cuvette, mixed and left for 1 min on ice. Electroporation was performed with a single pulse of 1.75 kV/cm, 200Ω and 50 µF (approx. time pulse 9.3 ms). Electroporated cells were gently mixed with 1 ml Eugon broth medium supplemented with 0.05% Tween80 and allowed to recover for 3.5 h at 26° C. and 220 rpm. Aliquots of 50 and 100 µl of the recovered cells were plated onto selective Eugon agar supplemented with 0.05% Tween80 and kanamycin (20 µg/ml). Transformants appeared after 7 days of incubation at 26° C.

A5 Unmarked Gene Deletion in *R. equi* Strains Using 5-fluorocytosine (5-Fc) Selection Unmarked gene deletion mutants of *R. equi* were made essentially as described (Van der Geize et al., 2008). *R. equi* transformants obtained from electroporation of wild type or mutant cells were streaked onto LB agar medium supplemented with apramycin to confirm apramycin resistance ($Apra^R$). Four $Apra^R$ transformants per transformation were grown overnight (20-24 h) at 30° C. and 200 rpm in 25 ml LB medium, and plated in $10^1$-$10^3$ fold dilutions in MM-Ac medium onto MM-Ac agar plates supplemented with 5-FC (100 µg/ml) in 100 µl aliquots. 5-FC resistant colonies, appearing after 3 days of incubation at 30° C., were replica streaked onto LB agar and LB agar supplemented with apramycin (50 µg/ml) to select for apramycin sensitive ($Apra^S$) and 5-FC resistant ($5-FC^R$) colonies. $Apra^S/5-FC^R$ colonies were checked for the presence of the desired gene deletion by colony PCR using primers amplifying the locus of the gene deletion (Table 5). Genomic DNA was isolated from potential gene deletion mutants and used to confirm the gene deletion using primers amplifying the ipdAB or ipdAB2 gene locus, as well as the upstream and downstream regions of these loci with primers as described in Table 5.

A6 Construction of Plasmids for ipdAB and ipdAB2 Gene Deletion in *R. equi*

Plasmid pSelAct-ipd1, for the generation of an unmarked gene deletion of the ipdAB operon in *R. equi* RE1, was constructed as follows. The upstream (1,368 bp; primers ipdABequiUP-F and ipdABequiUP-R) and downstream (1,396 bp; primers ipdABequiDOWN-F and ipdABequiDOWN-R) flanking regions of the ipdAB genes were amplified by PCR (Table 5, PCR1 and PCR2). The obtained amplicons were ligated into EcoRV digested pBluescript(II) KS, rendering plasmids pEqui14 and pEqui16 for the upstream and downstream region, respectively. A 1.4 kb SpeI/EcoRV fragment of pEqui14 was ligated into SpeI/EcoRV digested pEqui16, generating pEqui18. A 2.9 kb EcoRI/HindIII fragment of pEqui18, harboring the ipdAB gene deletion and its flanking regions, was treated with Klenow fragment and ligated into SmaI digested pSelAct suicide vector (Van der Geize et al., 2008). The resulting plasmid was designated pSelAct-ipd1 for the construction of ipdAB gene deletion mutant *R. equi* ΔipdAB (also referred to as RG1341). This mutant was deposited at the Collection Nationale de Cultures de Micro-organismes of the Institut Pasteur at Paris France under nr. CNCM I-4108.

Double gene deletion mutant *R. equi* ΔipdABΔipdAB2 (also referred to as RG2837) was made by unmarked gene deletion of the ipdAB2 operon in *R. equi* ΔipdAB mutant strain using plasmid pSelAct-ΔipdAB2. Plasmid pSelAct-ΔipdAb2 was constructed as follows. The upstream (1,444 bp; primers ipdAB2 equiUP-F and ipdAB2 equiUP-R) and downstream (1,387 bp; ipdAB2 equiDOWN-F, ipdAB2 equiDOWN-R) regions of ipdAB2 were amplified by PCR using genomic DNA as template (Table 5, PCR6 and PCR7). The amplicons were ligated into SmaI digested pSelAct, resulting in plasmids pSelAct-ipdAB2 equiUP and pSelAct-ipdAB2 equiDOWN, respectively. Following digestion with BglII/SpeI of both plasmids, a 1,381 bp fragment of pSelAct-ipdAB2 equiDOWN was ligated into pSelAct-ipdAB2 equiUP, resulting in pSelAct-ΔipdAB2 used for the construction of a ΔipdAB2 gene deletion. The resulting mutant *R. equi* ΔipdABΔipdAB2 was deposited at the Collection Nationale de Cultures de Micro-organismes of the Institut Pasteur at Paris France under nr. CNCM I-4109

A7 Construction of Plasmid for ipdAB Gene Deletion in *M. smegmatis* mc²155

Plasmid pK18-ipdABsmeg, used for the unmarked gene deletion of the ipdAB genes in *M. smegmatis* mc²155 was constructed as follows.

The upstream (1,502 bp; primers ipdABsmegUP-F and ipdABsmegUP-R) and downstream (1,431 bp; primers ipdABsmegDOWN-F and ipdABsmegDOWN-R) flanking regions of the ipdAB genes were amplified by PCR using genomic DNA of *M. smegmatis* mc²155 as template (Table 5, PCR12 and PCR13). The obtained amplicons were ligated into SmaI digested pK18mobsacB (Schäfer et al., 1994, *Gene* 145:69-73), resulting in pK18-ipdABsmegUP and pK18-ipdABsmegDOWN, respectively. A 1,5 kb DNA fragment obtained from BamHI/SpeI digested pK18-ipdABsmegUP was subsequently ligated into pK18-ipdABsmegUP linearized with BamHI/SpeI, resulting in the construction of pK18-ipdABsmeg used for ipdAB gene deletion.

A8 Construction of Plasmid for Gene Deletion of fadE30 in *R. equi*

Plasmid pSelAct-fadE30 for the generation of an unmarked gene deletion of fadE30 in *R. equi* RE1 was constructed as follows. The upstream (1,511 bp; primers fadE30 equiUP-F and fadE30 equiUP-R) and downstream (1,449 bp; primers fadE30 equiDOWN-F and fadE30 equiDOWN-R) flanking genomic regions of fadE30 were amplified by a standard PCR using High Fidelity DNA polymerase (Fermentas GmbH) (Table 5; PCR 15 and PCR 16). The obtained amplicons were ligated into the pGEM-T cloning vector (Promega Benelux), rendering pGEMT-fadE30UP and pGEMT-fadE30DOWN. A 1.4 kb BcuI/BglII DNA fragment was cut out of pGEMT-fadE30DOWN and ligated into BcuI/BglII linearized pGEMT-fadE30UP, resulting in pGEMT-fadE30. To construct pSelAct-fadE30, pGEMT-fadE30 was digested with NcoI and BcuI and treated with Klenow fragment. A 2.9 kb blunt-end DNA fragment, carrying the fadE30 gene deletion, was ligated into SmaI digested pSelAct (van der Geize et al., 2008). The resulting plasmid was designated pSelAct-fadE30 and used for the construction of mutant strain R. equi ΔfadE30.

A9 Construction of Plasmid for ipdAB Gene Deletion in N. seriola INS436

Plasmid pK18ipdABNser, used for unmarked gene deletion of the ipdAB genes in N. seriola INS436 was constructed as follows. The upstream (1,487 bp; primers ipdABNserUP-F and ipdABNserUP-R; PCR 24) and downstream (1,049 bp; primers ipdABNserDOWN-F and ipdABNserDOWN-R; PCR 25) flanking regions of the ipdAB genes were amplified by PCR using genomic DNA of N. seriola INS436 as DNA template (Table 5). The obtained amplicons were ligated into SmaI digested pK18mobsacB (Schäfer et al., 1994, in *Gene* 145: 69-73)), resulting in pK18-ipdABNserUP and pK18-ipdABNserDOWN, respectively. A 1.07 kb DNA fragment obtained from SmaI/PstI digested pK18-ipdABNserDOWN was subsequently ligated into pK18-ipdABNserUP which had been linearized with SmaI/PstI, resulting in the construction of plasmid pK18-ipdABNser that was used for ipdAB gene deletion.

A10 Construction of Mutant Strains R. equi ΔipdAB and R. equi ΔipdABΔipdAB2

R. equi unmarked gene deletion mutants of ipdAB (RG1341) and ipdABipdAB2 (RG2837) were constructed using a two-step homologous recombination strategy with 5-fluorocytosine counter-selection developed for R. equi (Van der Geize et al., 2008). For construction of the ΔipdAB mutant R. equi strain RG1341, the non-replicative plasmid pSelAct-ipd1 was mobilized to R. equi strain RE1 by electrotransformation. Four Apra$^R$ transformants, resulting from homologous recombination between plasmid pSelAct-ipd1 and the RE1 genome, were subsequently subjected to 5-FC selection in order to select for the occurrence of the second rare homologous recombination event resulting in gene deletion. Eighteen randomly picked Apra$^S$/5FC$^R$ colonies were subjected to colony PCR and three FC$^R$/Apra$^S$ colonies gave an amplicon of the expected size (296 bp, Table 5, PCR5). Genomic DNA was isolated from these three ΔipdAB mutants and subjected to PCR analysis of the ipdAB locus and its up- and downstream flanking regions (Table 5, PCR3 and PCR4). This analysis confirmed the presence of a genuine ipdAB gene deletion in two out of three cases and revealed no aberrant genomic rearrangements at the ipdAB locus. The presence of vapA as a marker of the virulence plasmid was confirmed by PCR (Table 5, PCR11). One ipdAB mutant strain was chosen, designated R. equi RG1341, and was used for further work.

Double gene deletion mutant strain RG2837 was constructed from strain RG1341 using plasmid pSelAct-ΔipdAB2 essentially as described for the isolation of the ΔipdAB single mutant. Four Apra$^R$ transformants, obtained from electroporation of cells of strain RG1341 with pSelAct-ΔipdAB2, were subjected to 5-FC selection to select for Apra$^S$/5-FC$^R$ colonies. Subsequent PCR analysis of eighteen Apra$^S$/5-FC$^R$ colonies confirmed that two colonies harbored a ΔipdAB2 gene deletion, as evident from the obtained 123 bp amplicon using oligonucleotide developed to amplify the ipdAB2 operon (Table 5, PCR10). Further analysis of the upstream and downstream regions of the ipdAB2 locus by PCR confirmed the presence of an ipdAB2 gene deletion and revealed no aberrant genomic rearrangements (Table 5, PCR8 and PCR9). Also, the presence of the vapA virulence gene was confirmed by PCR (Table 5, PCR11). One ΔipdABΔipdAB2 double gene deletion mutant strain RG2837 was chosen for further work.

A11 Construction of Mutant Strain M. smegmatis ΔipdAB

An unmarked ipdAB gene deletion mutant of M. smegmatis mc$^2$155 was constructed using the sacB counter selection system (Pelicic et al., 1996, *Mol. Microbiol.* 20:919-925; Van der Geize et al., 2001, *FEMS Microbiol Lett.* 205:197-202) as follows. For construction of the ΔipdAB mutant of M. smegmatis strain mc$^2$155, the non-replicative plasmid pK18-ipdABsmeg was mobilized to M. smegmatis by electrotransformation. Several transformants were obtained. One kanamycin resistant transformant was grown for 2 days at 37° C. non-selectively in TSB medium containing 0.05% Tween80 and subsequently plated onto TSB agar plates containing 2% sucrose to select for kanamycin sensitive (Km$^S$) and sucrose resistant (Suc$^R$) double-recombinants by sacB counter-selection. Colonies appearing after 3 days of incubation were replica streaked onto TSB agar and TSB agar supplemented with kanamycin (10 μg/ml) to select for Km$^S$/Suc$^R$ colonies. Genuine Km$^S$/Suc$^R$ colonies were further checked by colony PCR for the presence of the ipdAB gene deletion (Table 5, PCR14). Genomic DNA was isolated from three potential ipdAB mutants. PCR analysis confirmed the presence of the ipdAB gene deletion, and one ipdAB mutant strain was chosen for further work and designated M. smegmatis ΔipdAB.

A12 Construction of Mutant Strain R. equi ΔfadE30

An unmarked gene deletion of fadE30 in R. equi RE1 was generated using a two-step homologous recombination strategy with 5-fluorocytosine counter-selection developed for R. equi (Van der Geize et al., 2008). For construction of the ΔfadE30 mutant strain, the non-replicative plasmid pSelAct-fadE30 was mobilized to R. equi strain RE1 by electrotransformation. Two Apra$^R$ transformants, resulting from homologous recombination between plasmid pSelAct-fadE30 and the RE1 genome, were subsequently subjected to 5-FC selection in order to select for the occurrence of the second rare homologous recombination event resulting in fadE30 gene deletion. Eighteen randomly picked Apra$^S$/5FC$^R$ colonies were subjected to colony PCR using primers fadE30cont-F and fadE30cont-R (Table 5; PCR 19) and thirteen FC$^R$/Apra$^S$ colonies gave an amplicon of the expected size (428 bp). Genomic DNA was isolated from two potential ΔfadE30 mutants and subjected to PCR analysis. PCR analysis of the fadE30 locus, using oligonucleotide primers fadE30contr-F and fadE30contr-R (Table 5), confirmed the presence of a fadE30 gene deletion and the absence of the wild type fadE30 gene. Analysis of the upstream and downstream flanking regions by PCR resulted in the expected 1.86 kb and 1.76 kb products, respectively. The analysis confirmed the presence of a genuine fadE30 gene deletion in both cases and revealed no aberrant genomic rearrangements at the fadE30 locus. The presence of vapA as a marker for the virulence plasmid was confirmed by PCR. One fadE30 mutant strain was designated R. equi ΔfadE30 and was used for further work.

A13 Construction of Mutant Strain N. seriola ΔipdAB

An unmarked ipdAB gene deletion mutant of N. seriola INS436 was constructed using the sacB counter selection system (Pelicic et al., 1996, in *Mol. Microbiol.* 20:919-925; Van der Geize et al., 2001, in *FEMS Microbiol Lett.* 205:197-202) as follows. The non-replicative plasmid pK18-ipdABNser was mobilized to N. seriola INS436 by electrotransformation. Several kanamycin resistant transformants were then grown non-selectively for 7 days at 26° C. in Eugon broth medium containing 0.05% Tween80. Selection for kanamycin sensitive ($Km^S$) and sucrose resistant ($Suc^R$) double-recombinants by sacB counter-selection was subsequently performed by plating onto Eugon agar plates containing 2% sucrose. Colonies appearing after 7 days of incubation at 26° C. were replica picked onto Eugon agar plates and Eugon agar plates supplemented with kanamycin (20 μg/ml), to select for $Km^S/Suc^R$ colonies. Genuine $Km^S/Suc^R$ colonies were further checked by colony PCR for the presence of the ipdAB gene deletion using primers ipdABNser-F and ipdABNser-R (Table 5). Genomic DNA was isolated from three potential ipdAB mutants. PCR analysis using primer pair ipdABNser-F and ipdABNser-R(PCR 23) resulted in a 222 bp PCR product and the absence of a wild type 1,634 bp PCR product confirming the presence of the ipdAB gene deletion. Primer pair IpdABNser-F2 and IpdABNserDOWN-Contr-R (PCR 26) was used to further confirm the ipdAB gene deletion. This primer pair resulted in an expected PCR product of 1,148 bp for the ipdAB mutant, whereas a 2,560 bp PCR product was obtained only for the wild type strain. One mutant strain was designated N. seriola ΔipdAB and chosen for further work.

Part B: Macrophage Survival as a Model for In Vivo Attenuation
B1 Used Strains
Virulent Strains Strain RE1: wildtype parent strain. This strain grows on cholesterol.

Strain RE1ΔsupAB: deletion of supAB gene. This strain is unable to grow on cholesterol.
Non-virulent strain Strain 103−: lacks the 80- to 90-kb virulence plasmid and is known to be apathogenic in horses (Takai et al. 2000, Infect. Immun. 68: 6840-6847.). This strain grows on cholesterol.
Strains According to the Invention Strain RE1ΔipdAB (RG1341): the ipdAB gene in the cholesterol catabolic cluster is deleted. This strain does not grow on 4-androstene-3,17-dione (AD).

Strain RE1ΔipdAB-AD+: bacteria of strain RE1ΔipdAB adapted to grow on AD (if strain RE1ΔipdAB is plated in high concentration (more than $10^6$ CFU/ml) with AD as the sole carbon source, then a few colonies may arise that do grow on AD).

Strain RE1ΔipdABipdAB2 (RG2837): second set of ipdAB genes (not part of the cholesterol catabolic cluster) is also deleted. This strain does not grow on AD.

Strain R. equi ΔfadE30. This strain is severly impaired for growth on HIP/HIL and AD.
B2 Rhodococcus equi Cultures for Macrophage Infection The different Rhodococcus equi strains to be tested in the macrophage survival assay were grown overnight (17 h) at 37° C. and 100 rpm in Nutrient Broth (Difco) aiming on a final concentration of $1-2×10^8$ CFU/ml. Only freshly prepared cultures were used. After inoculation of the macrophages, a live count determination was done (plate counting) in order to confirm the infectivity titer.
B3 Rhodococcus Cultures for Foal Challenge Rhodococcus equi strain RE1, RE1ΔipdAB and RE1ΔipdAB-AD+ were plated on blood agar and incubated for 24 hours at 37° C. Bacteria were harvested with 4 ml of sterile isotonic PBS per plate. The bacterial suspension was diluted with sterile isotonic PBS aiming at a final concentration of $4×10^4$ CFU/ml. Transport was at ambient temperature; the diluted cultures were used within 4 hours after preparation. After challenge, a live count determination was done (plate counting) in order to confirm the infectivity titer. The live counts were $4.35×10^4$ CFU/ml for RE1, $7.1×10^4$ CFU/ml for RE1ΔipdAB and $5.8×10^4$ CFU/ml for RE1ΔipdAB-AD+, respectively.

B4 Test Systems
Macrophage Cell Line

Cell line U937 (human monocyte) was used to test for survival of Rhodococcus equi strains. The monocytes were grown in RPMI 1640+$NaHCO_3$+NAPYR+ glucose medium (RPMI 1640 medium), buffered with 10 mM HEPES and supplemented with 200 IU/ml penicillin and streptomycin and 10% fetal bovine serum (FBS). The cells were grown in suspension at 37° C. and 5% $CO_2$.
Foals Eight foals were used: seven 3 to 5-week-old foals and one 7 week-old (all with mare). The foals were allotted to three groups of 3, 3 and 2 foals, reckoning an even distribution of age over the groups. Housing was in isolation facilities. During the experiment the foals sucked and the mares were fed according to standard procedures. Fresh tap water was available ad libidum

| Group | Mare | Foal ID No | Date of birth | gender |
|---|---|---|---|---|
| RE1 | 5977 | 17 | May 10, 2008 | male |
| | 9263 | 18 | May 17, 2008 | female |
| | 1952 | 19 | Apr. 19, 2008 | male |
| RE1ΔipdAB | 6095 | 20 | May 02, 2008 | female |
| | 3071 | 21 | May 10, 2008 | male |
| | 9390 | 22 | May 20, 2008 | male |
| RE1ΔipdAB-AD+ | 8719 | 23 | May 09, 2008 | male |
| | 4983 | 24 | May 10, 2008 | male |

At T=0 all foals were challenged intratracheally with 100 ml challenge culture of strain RE1, RE1ΔipdAB or RE1ΔipdAB-AD+ (see here above under "Rhodococcus cultures for foal challenge") using a syringe with needle, so called trans-tracheal injection.
B5 Experimental Procedures and Parameters
Macrophage Survival Test For the macrophage survival assay, monocytes were grown for several days as described herein before. The culture medium was replaced with fresh culture medium and the cells were activated overnight with 60 ng/ml phorbol 12-myristate 13-acetate (PMA) to induce their differentiation to macrophages.

The differentiated cells were spun down (5 min. at 200×g) and the pellet was re-suspended in fresh, antibiotic free RPMI 1640 medium with 10% FBS. For each strain to be tested, a tube containing 10 ml of a cell suspension with approximately $10^6$ cells/ml was inoculated with Rhodococcus equi at a multiplicity of infection (MOI) of approximately 10 bacteria per macrophage.

The bacteria were incubated with the macrophages for 1 hour at 37° C. and 5% $CO_2$. The medium was replaced with 10 ml RPMI 1640 medium supplemented with 10% FBS and 100 μg/ml gentamycin and incubated again for 1 hour to kill any extracellular bacteria. The macrophages (with internalized R. equi) were spun down (5 min. at 200×g) and the pellet was re-suspended in 40 ml RPMI 1640 medium, buffered with 10 mM HEPES and supplemented with 10% FBS and 10 μg/ml gentamycine. This suspension was divided over 4 culture bottles (10 ml each) and incubated at 37° C. and 5% $CO_2$. After 4, 28, 52 and 76 hours the macrophages (one culture bottle per strain) were spun down (5 min. at 200×g) and the pellet washed twice in 1 ml antibiotic free RPMI 1640 medium. Finally the pellet was lysed with 1% Triton X-100 in 0.01M phosphate buffered saline (PBS), followed by live count determination (plate counting).

Foal Challenge

1—Rectal temperature: measured day 1 before challenge, day of challenge (just before challenge) and then once daily after challenge until necropsy. 2—Clinical examination: during 3 weeks post-challenge the horses were daily examined for clinical signs.

3—Post mortem examination and bacteriology: on day 21 post-challenge the foals were weighed and then killed by anesthesia with xylazine (100 mg/100 kg) and ketamine (500 mg/100 kg) and subsequent bleeding to death. The lungs were weighed in order to calculate the lung to body weight ratio. A complete post-mortem examination was performed with special attention to the lungs and associated lymph nodes. In case of abnormalities, samples for histology were taken as deemed necessary by the pathologist.

Tissue samples (1 cm$^3$) were excised from seven standard sites representative of the lobes of each half of the lung (3 sites per half+accessory lobe); diseased tissue was preferentially selected for each site, if it was present. The mirror image samples (the two samples of the equivalent lobe on each half) were pooled to give 3 samples per foal+a sample of the accessory lobe. Each (pooled) sample was homogenized, serially diluted and inoculated on blood agar plates and then incubated at 37° C. for 16-24 hours. *Rhodococcus* colonies were enumerated and expressed as CFU/ml homogenate. Additional swabs were taken from all other abnormalities. Swabs were streaked on blood agar plates and then incubated at 37° C. for 16-24 hours. *Rhodococcus equi* was initially identified by its typical non-hemolytic mucoid colony morphology. Further identification was done by Gram stain, API/Phoenix, and/or PCR.

B6 Results

Survival in Macrophages

Figure 1:
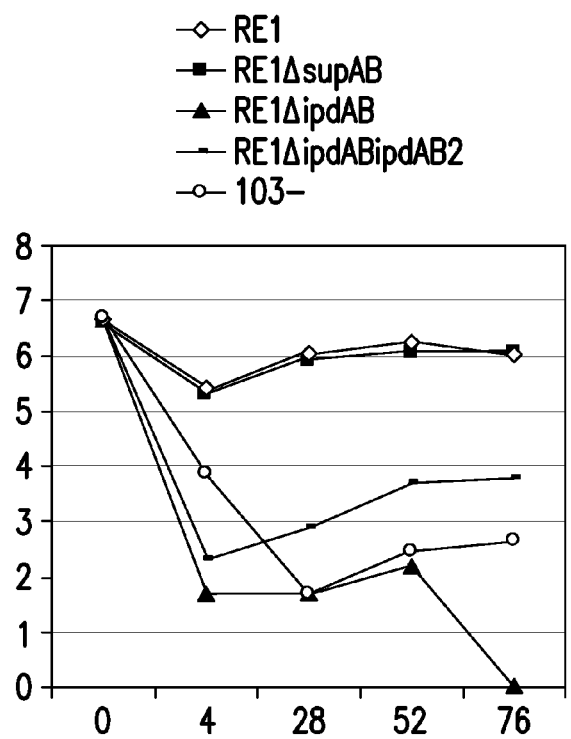
FIG. 1: Survival of various *R. equi* mutants in macrophages.
Figure 2:
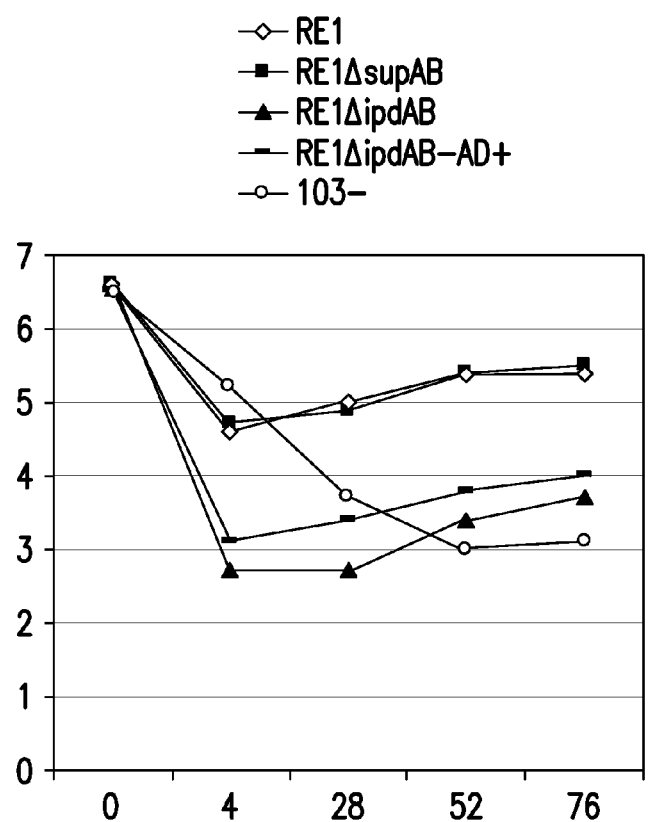
FIG. 2: Survival of various R. equi mutants in macrophages.
Figure 4:
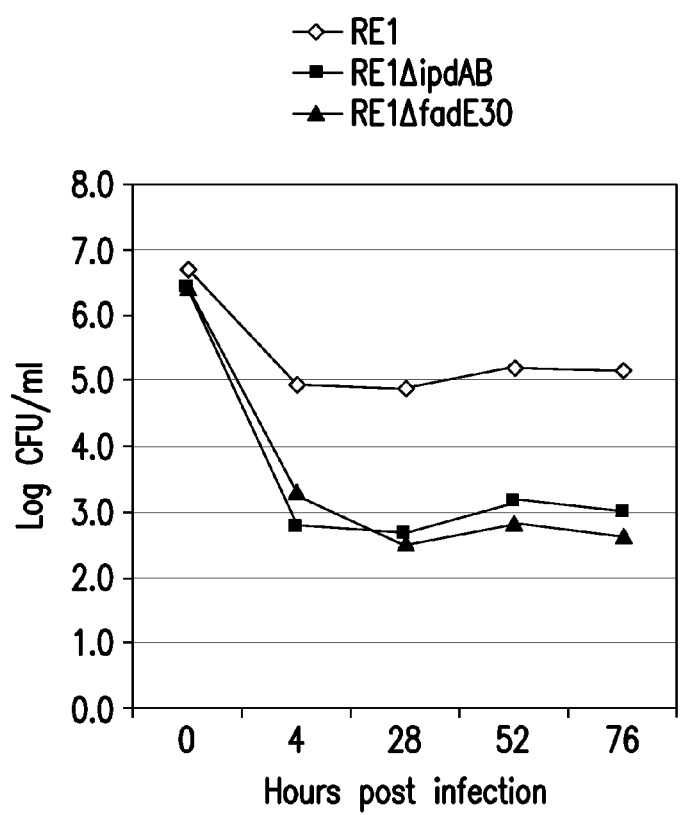
FIG. 4: Survival of various R. equal mutants in macrophages.

The results of two separate experiments are shown in Table 1 (in conjunction with FIGS. 1) and 2 (in conjunction with FIG. 2). The results show that the RE1ΔsupAB mutant is able to survive in macrophages in a similar manner as the wild type parent strain RE1, indicating that cholesterol metabolism is not essential for macrophage survival. This is in line with the recognition that cholesterol metabolism as such is not important for virulence. In contrast, survival in macrophages of strain RE1ΔipdAB, strain RE1ΔipdABipdAB2, strain RE1ΔipdAB-AD+ and strain 103–, was clearly reduced. Note however that the bacteria are still able to survive in the macrophages but at a significantly reduced level (typically at a concentration of 100 to 1000 times below the wild-type level). Strain 103– lacks the 80- to 90-kb virulence plasmid and is known to be avirulent in horses (Takai et al.). This strain 103– is not suitable as a vaccine strain since it does not induce a protective immune response, probably because it lacks the virulence plasmid. In Table 9 (in conjunction with FIG. 4) the results are shown for mutant strain *R. equi* ΔfadE30 in comparison with the wild-type strain RE1 and strain RE1ΔipdAB. Clearly the fadE30 mutant has a survival characteristic comparable to the ΔipdAB strain, and is also less capable of surviving in the macrophages.

TABLE 1

Survival of *R. equi* mutants in macrophages

| | log CFU/ml at . . . hours post-infection | | | | |
|---|---|---|---|---|---|
| strain | 0 | 4 | 28 | 52 | 76 |
| RE1 | 6.7 | 5.4 | 6.1 | 6.2 | 6.0 |
| RE1ΔsupAB | 6.6 | 5.3 | 5.9 | 6.1 | 6.1 |
| RE1ΔipdAB | 6.6 | 1.7 | 1.7 | 2.2 | 0 |
| RE1ΔipdABipdAB2 | 6.7 | 2.3 | 2.9 | 3.7 | 3.8 |
| 103– | 6.7 | 3.9 | 1.7 | 2.5 | 2.7 |

TABLE 2

Survival of *R. equi* mutants in macrophages

| | log CFU/ml at . . . hours post-infection | | | | |
|---|---|---|---|---|---|
| strain | 0 | 4 | 28 | 52 | 76 |
| RE1 | 6.6 | 4.6 | 5.0 | 5.4 | 5.4 |
| RE1ΔsupAB | 6.6 | 4.7 | 4.9 | 5.4 | 5.5 |
| RE1ΔipdAB | 6.6 | 2.7 | 2.7 | 3.4 | 3.7 |
| RE1ΔipdAB-AD+ | 6.5 | 3.1 | 3.4 | 3.8 | 4.0 |
| 103– | 6.5 | 5.2 | 3.7 | 3.0 | 3.1 |

The results with strains that have a mutation in the operon that encodes a protein involved in methylhexahydroindanedione propionate degradation activity (i.e. strains RE1ΔipdAB, RE1ΔipdABipdAB2, RE1ΔipdAB-AD+ and *R. equi* ΔfadE30) show that these strains are less capable to survive in macrophages, in particular, their survival capabilities are comparable to the survival capabilities of the apathogenic strain 103–. This already is a good indication of adequate attenuation. Strain RE1ΔipdAB-AD+ demonstrated the same macrophage phenotype as strain RE1ΔipdAB indicating that it is an intact ipdAB operon rather than an intact cholesterol metabolism that is essential for macrophage survival at the wild-type level. The single ipdAB gene deletions (in the cholesterol catabolic gene cluster) resulted in a hampered macrophage survival. An additional deletion in a copy of these genes (ipdA and ipdB outside the cholesterol catabolic cluster, called ipdA2 and ipdB2) had no further attenuating effect in the macrophage test.

Given these results, strains RE1ΔipdAB and RE1ΔipdAB-AD+ (=strain RE1ΔipdAB adapted to growth on AD) were administered intratracheally to foals (normal challenge procedure) and compared with the wildtype parent strain RE1 to test for in vivo attenuation.

TABLE 9

Survival of *R. equi* mutants in macrophages

| | log CFU at . . . hours post-infection | | | | |
|---|---|---|---|---|---|
| strain | 0 | 4 | 28 | 52 | 76 |
| RE1 | 6.7 | 4.9 | 4.9 | 5.2 | 5.2 |
| RE1 ΔipdAB | 6.4 | 2.8 | 2.7 | 3.1 | 3.0 |
| RE1 ΔfadE30 | 6.4 | 3.3 | 2.5 | 2.8 | 2.6 |

Rectal Temperature

In table 3 (in conjunction with FIG. 3) the results of the rectal temperature are presented. Group 1 is the Group that received the wild-type RE1 strain. Groups 2 and 3 received the RE1ΔipdAB and RE1ΔipdAB-AD+ respectively. The temperatures of days 3 to 10 are not shown since they did not reveal any significant changes from normal rectal temperature. Abnormal temperatures are indicated in bold. Two of three foals (no. 18 and 19) challenged with the wild type parent strain RE1 showed clearly increased rectal temperatures from 14 days post-challenge onwards. The increase in rectal temperature after 14 days coincided with the development of clinical signs (see below). Foal no. 21 (challenged with strain RE1ΔipdAB) showed a slightly increased temperature (39.1° C.) at 1 day post-challenge which most probably is not related to Rhodococcus infection (incubation time in this challenge model normally is >7 days). Further no increased temperatures were observed in the RE1ΔipdAB or RE1ΔipdAB-AD+ challenged foals.

TABLE 4

Lung scores
% consolidation / pneumonia per lung lobe

| group | foal no | apical L | apical R | caudal L | caudal R | accessory | total |
|---|---|---|---|---|---|---|---|
| RE1 | 17 | 5 | 30 | 5 | 30 | 30 | 100 |
|  | 18 | 10 | 0 | 60 | 40 | 70 | 180 |
|  | 19 | 50 | 70 | 50 | 70 | 90 | 330 |
|  | mean | 22 | 33 | 38 | 47 | 63 | 203 |

TABLE 3

Rectal temperature post-challenge

| group | foal no | -1 | 0 | 1 | 2 | 11 | 12 | 13 | 14 | 15 | 16 | 17 | 18 | 19 | 20 | 21 |
|---|---|---|---|---|---|---|---|---|---|---|---|---|---|---|---|---|
| RE1 | 17 | 38.5 | 38.4 | 38.6 | 38.4 | 38.3 | 38.3 | 38.2 | 38.3 | 38.5 | 38.6 | 38.6 | 38.7 | 38.6 | 38.5 | 38.2 |
|  | 18 | 38.5 | 38.4 | 38.5 | 38.3 | 38.4 | 38.5 | 38.3 | 38.2 | 38.6 | 38.6 | 39.4 | 39.9 | 40.4 | 40.4 | 40.3 |
|  | 19 | 38.3 | 38.0 | 38.6 | 37.9 | 38.4 | 38.7 | 38.7 | 39.1 | 39.1 | 38.8 | 39.7 | 39.6 | 39.1 | 38.8 | 38.0 |
|  | mean | 38.4 | 38.3 | 38.6 | 38.2 | 38.4 | 38.5 | 38.4 | 38.5 | 38.7 | 38.7 | 39.2 | 39.4 | 39.4 | 39.2 | 38.8 |
| RE1ΔipdAB | 20 | 38.5 | 38.5 | 38.8 | 38.4 | 38.5 | 38.2 | 38.4 | 38.2 | 38.4 | 38.3 | 38.1 | 38.5 | 38.4 | 38.4 | 38.4 |
|  | 21 | 38.6 | 37.9 | 39.1 | 38.4 | 38.3 | 38.2 | 38.3 | 38.4 | 38.6 | 38.0 | 38.2 | 38.3 | 38.0 | 38.1 | 38.1 |
|  | 22 | 38.5 | 38.6 | 38.7 | 38.5 | 38.4 | 38.2 | 38.4 | 38.4 | 38.4 | 38.4 | 38.4 | 38.5 | 38.5 | 38.4 | 38.5 |
|  | mean | 38.5 | 38.3 | 38.9 | 38.4 | 38.4 | 38.2 | 38.4 | 38.3 | 38.5 | 38.2 | 38.2 | 38.4 | 38.3 | 38.3 | 38.3 |
| RE1ΔipdAB-AD+ | 23 | 38.8 | 38.2 | 38.7 | 38.2 | 38.5 | 38.5 | 38.4 | 38.2 | 38.4 | 38.5 | 38.6 | 38.2 | 38.1 | 38.2 | 38.0 |
|  | 24 | 38.5 | 38.2 | 38.5 | 38.1 | 38.3 | 38.3 | 38.2 | 38.2 | 38.1 | 38.2 | 38.2 | 38.1 | 38.0 | 38.1 | 37.9 |
|  | mean | 38.7 | 38.2 | 38.6 | 38.2 | 38.4 | 38.4 | 38.3 | 38.2 | 38.3 | 38.4 | 38.4 | 38.2 | 38.1 | 38.2 | 38.0 |

Clinical Signs Post-challenge

Clinical scores from day 7 to 21 indeed showed that foal no. 18 and 19, challenged with wild type parent strain RE1 developed signs of respiratory disease from 13 days post-challenge onwards. Foal no. 17 (also RE1 challenge group) showed only mild clinical signs post-challenge. The foals which were challenged with mutant strain RE1ΔipdAB and RE1ΔipdAB-AD+ showed no clear signs of respiratory disease. The clinical effects of the latter two groups were mainly based on a slightly increased heart beat, which also (in part) could be due to handling stress, since it was also present before challenge.

Post-mortem Examination

The post-mortem findings with respect to the lungs are shown in Table 4. After challenge with the wild type parent strain RE1 the foals developed signs of respiratory disease (in particular foal no. 18 and 19). The foals challenged with mutant strains remained healthy. At 21 days post-challenge the foals were killed and necropsied. At post-mortem all foals challenged with the wildtype strain appeared to have typical pyogranulomatous pneumonia from which R. equi was re-isolated as a pure culture and the identity of the wildtype strain was confirmed by PCR. From foal no. 18 wild-type R. equi was also isolated from an enlarged mediastinal lymph node.

The lungs of the foals challenged with the mutant strains did not show pneumonic areas and Rhodococcus was not isolated, except from a slightly enlarged bronchial lymph node of foal no. 20, and from healthy lung tissue of foal no. 24. The identity of these isolates was confirmed as RE1ΔipdAB and RE1ΔipdAB-AD+ by PCR and growth on AD agar, respectively.

TABLE 4-continued

Lung scores
% consolidation / pneumonia per lung lobe

| group | foal no | apical L | apical R | caudal L | caudal R | accessory | total |
|---|---|---|---|---|---|---|---|
| RE1ΔipdAB | 20 | 0 | 0 | 0 | 0 | 0 | 0 |
|  | 21 | 0 | 0 | 0 | 0 | 0 | 0 |
|  | 22 | 0 | 0 | 0 | 0 | 0 | 0 |
|  | mean | 0 | 0 | 0 | 0 | 0 | 0 |
| RE1ΔipdAB-AD+ | 23 | 0 | 0 | 0 | 0 | 0 | 0 |
|  | 24 | 0 | 0 | 0 | 0 | 0 | 0 |
|  | mean | 0 | 0 | 0 | 0 | 0 | 0 |

B7 Conclusion for Part B of the Experiments

Strains RE1ΔipdAB and RE1ΔipdAB-AD+ are clearly impaired in macrophage survival and are attenuated in foals. Knocking out the second copy of the ipdAB gene (resulting in RE1ΔipdABipdAB2) did not seem to have an additional effect in the macrophage survival test and probably also not in foals. The combined in vivo and in vitro results with strains RE1, RE1supAB, 103−, RE1ΔipdAB and RE1ΔipdAB-AD+ indicate a good correlation between macrophage survival level and in vivo virulence for a bacterium belonging to the nocardioform actinomycetes. In particular, it appears that when a mutant strain has significantly reduced macrophage survival capabilities, typically about 2 to 3 logs with respect to the virulent parent strain, then the mutant strain is significantly attenuated with respect to the parent strain.

Based on the commonly known fact that the way of infection and virulency factors is shared among nocardiofrom Actinomycetes—hence the fact that Rhodococcus equi is commonly used as a model to study Mycobacteriaceae, in particular with respect to the virulence factors related to macrophage survival and persistency (see i.a. PNAS, Feb. 6, 2007, vol. 104, no. 6, pp 1947-1952)—it is understood that the reduced survival rate for bacteria by inactivation of a gene that encodes a protein involved in methylhexahydroindanedione propionate degradation, is generic for attenuation of nocardioform actinomycetes.

Part C: Efficacy of Mutant Bacterium in Protection Against Infection with Wild-Type C1 Introduction The efficacy with respect to a pharmaceutical composition containing live mutant bacteria according to the present invention is believed to be inherent. This can be understood by recognizing that the publicly available knowledge about mutations in the cholesterol metabolism clearly indicates that bacteria having mutations in the cholesterol metabolism still have an antigenic load comparable with that of wild-type organisms. In combination with the current knowledge, made available by the present invention, that the mutant live bacteria are still able to enter the macrophages and persist in them, it leaves no doubt that the stimulus of an immune response is secured. Still, applicant has conducted experiments to confirm this believe. For this, a vaccine containing live *Rhodococcus equi* was used. On itself, there is still no vaccine available against this bacterium which makes the experiments inherently relevant. But more importantly, this bacterium has been commonly recognised as a good model for other nocardiofrom actinomycetes, in particular *Mycobaterium tuberculosis*. Other confirming experiments (to obtain confirmatory results cover the complete range of nocardioform actinomycetes), could for example be done with *Nocardia seriolae* (see paragraph C6). This is a typical fish pathogen against which no adequate vaccine is available for the same reasons as why there is no adequate vaccine available against other macrophage surviving nocardioform actinomycetes.

C2 Experimental Design

Sixteen 2 to 4-week-old foals were used for the study. The foals were divided in four groups of 4 foals and vaccinated orally with 1 ml vaccine containing different doses of RE1ΔipdAB (constituted in sterile isotonic phosphate buffered saline) Group 1 was vaccinated with $5\times10^9$ CFU, group 2 was vaccinated with $5\times10^8$ CFU; group 3 was vaccinated with $5\times10^7$ CFU and group 4 was left as unvaccinated controls. Vaccinations were given at T=0 and at T=2 weeks. At T=4 weeks all foals were challenged intratracheally with 100 ml culture of virulent *Rhodococcus equi* strain 85F (containing $5\times10^6$ CFU per 100 ml dose).

During a period of 3 weeks after challenge the horses were clinically evaluated. The foals were weighed at day of first vaccination, day of challenge and at day of necropsy. At 3 weeks after challenge (or earlier in case of severe clinical signs) the foals were weighed and euthanized and a complete post-mortem examination was performed with special attention to the lungs and respiratory lymph nodes. The lungs were weighed in order to calculate the lung to body weight ratio. Tissue samples from all lung lobes were sampled for examination.

C3 Materials and Methods

Test Articles

The vaccine contained live *Rhodococcus* of strain RE1ΔipdAB, constituted in sterile isotonic phosphate buffered saline (PBS). The challenge culture was made as follows: *Rhodococcus equi* strain 85F was plated on blood agar and incubated for 24 hours at 37° C. Bacteria were harvested with 4 ml of sterile isotonic PBS per plate. The bacterial suspension was diluted with sterile isotonic PBS aiming on a final concentration $4\times10^4$ bacteria/ml. Transport was at ambient temperature; diluted culture was used within 4 hours after preparation. After challenge, a live count determination was done in order to confirm the infectivity titer. The titer was $5.3\times10^4$ CFU/ml.

Experimental Procedures and Parameters

Bacterial reisolation was performed by sampling rectal swabs just before each vaccination and on day 0, 1, 2, 3, 6, 10, 14, 15, 16, 17, 20 and 24 (after vaccination). Nasal swabs were sampled from the foals at T=0 (just before first vaccination). The swab samples were serially diluted in physiological salt solution and plated on bloodagar and incubated at 37° C. for 16-24 hours. *Rhodococcus* colonies were initially identified by the typical non-hemolytic mucoid colony morphology, enumerated and expressed as CFU/ml. On each isolation day three re-isolates were selected at random (from three different horses if present) were used to confirm the identity: Gram stain, API/Phoenix and PCR on ipdAB genes.

During the study the horses were daily observed for any abnormalities of general health and/or behavior by a biotechnician. Starting one day before challenge the horses were daily examined (until necropsy) for clinical signs. Weighing took place just before first vaccination, just before challenge and just before necropsy. This way, the weight gain and the lung to body weight ratio could be calculated.

On day 14-20 post-challenge (or earlier in case of severe clinical signs) the foals were killed by anesthesia with xylazine (100 mg/100 kg) and ketamine (500 mg/100 kg) and subsequent bleeding to death. The lungs were weighed in order to calculate the lung to body weight ratio. A complete post-mortem examination was performed. Tissue samples (1 $cm^3$) were excised from seven standard sites representative of the lobes of each half of the lung (3 sites per half+accessory lobe); diseased tissue was preferentially selected for each site, if it was present. The mirror image samples (the two samples of the equivalent lobe on each half) were pooled to give 3 samples per foal+a sample of the accessory lobe. Each (pooled) sample was homogenized, serially diluted and inoculated on blood agar plates and then incubated at 37° C. for 16-24 hours. *Rhodococcus* colonies were enumerated and expressed as CFU/ml homogenate. The pneumonia lung score for each animal was obtained by establishing for the apical (left+right), caudal (left+right) and accessory lung nodes the percentage of consolidation. For each animal, these percentages were added to obtain one lung score figure. This way, a lung score between 0 and 500 is obtained.

C4 Results

The post-challenge results are summarized in Table 7. From the summarized results it is clear that all four controls developed severe signs of pyogranulomatous pneumonia caused by *R. equi* as the sole pathogen. Two vaccinates no. 4 and 5 had signs comparable to the controls but all other vaccinates had much milder signs or virtually no signs. The % lung weight (an objective measure for the amount of pneumonia) confirms the partial protection in most of the vaccinates.

Vaccinated foal no. 2 had pneumonia caused by aspecific bacteria. In fact this foal can be regarded as protected since *Rhodococcus* was not isolated despite the massive challenge. In addition, from three vaccinated foals with pneumonia, mixed infections were isolated. These mixed infections probably have negatively influenced the different protection parameters. Although the protective effect of the vaccine is evident, no dose response effect was observed. In fact, the lowest dose appeared to provide the best results. Based on this, in conjunction with the fact that foals have an immature gastrointestinal flora, it is believed that an optimum dose lies between $1\times10^4$ and $1\times10^{10}$ CFU.

TABLE 7

Summary results after challenge

| group | foal no | daily weight gain after challenge | % lung weight per total weight at post-mortem | pneumonia lung score | mean isolation R. equi from lung log$_{10}$ CFU/ml |
|---|---|---|---|---|---|
| group 1 | 1 | 0.24 | 1.6% | 126 | 4.75 |
|  | 2 | 0.06$^a$ | 1.4%$^a$ | 25$^a$ | 0 |
|  | 3 | 0.24 | 1.2% | 14 | 0.98 |
|  | 4 | 0.31 | 1.9% | 211 | 5.88 |
|  | mean | 0.26 | 1.6% | 117 | 2.90 |
| group 2 | 5 | −0.06 | 3.1% | 335 | 7.09 |
|  | 6 | 0.45 | 1.1% | 8 | 1.24 |
|  | 7 |  |  |  |  |
|  | 8 | 0.18 | 1.9% | 166 | 5.34 |
|  | mean | 0.19 | 2.0% | 170 | 4.56 |
| group 3 | 9 | 0.25 | 1.4% | 95 | 2.36 |
|  | 10 | 0.44 | 1.0% | 4 | 0 |
|  | 11 | 0.27 | 1.2% | 93 | 2.82 |
|  | 12 | 0.31 | 1.1% | 0 | 0 |
|  | mean | 0.31 | 1.2% | 48 | 1.30 |
| controls | 13 | 0.13 | 2.6% | 320 | 8.82 |
|  | 14 | 0.21 | 2.0% | 230 | 6.96 |
|  | 15 | 0.10 | 3.4% | 300 | 8.91 |
|  | 16 | 0.01 | 2.9% | 230 | 5.91 |
|  | mean | 0.11 | 2.7% | 270 | 7.65 |

C5 Conclusion for Part C of the Experiments

All three oral doses of the vaccine appeared to be safe for young foals and induced substantial protection against a severe intratracheal challenge. In the current experiments the genes ipdA and ipdB of the ipdAB operon were both removed from the genome of the bacteria in the vaccine. It is clear however that other mutations involving the same operon can be equally effective. A mutation which for example affects only one of the genes ipdA or ipdB can be equally effective per se. In any of the latter cases, the transferase involved cannot be made and thus the same phenotype is arrived at. Indeed this can also be derived from Rengarajan (PNAS, Jun. 7, 2005, Vol. 102, No. 23, pp 8327-8332). In this reference relevant proof is provided for another nocardioform actinomycete, viz. *Mycobacterium tuberculosis*: inactivating either one of the orthologous ipd genes (called rv3551 and rv3552 respectively in *M. tuberculosis*) results in the same phenotype.

C6 Confirmation of Vaccine Efficacy of a *Nocardia seriolae* Mutant

The above experiments for *Rhodococcuse equi* were repeated for another actinomycete, the fish pathogen *Nocardia seriolae*, which causes nocardiosis in fish. For this experiment the wildtype strain INS436 and the ΔipdAB strain as mentioned here-above in parargraph A13 were used.

Groups of 20 yellowtail fish (*Seriola quinqueradiata*) were IP-injected with either the wild-type strain or mutant strain (at various concentrations), and one group of 20 fish was left as control. The fish were observed for the occurence of mortality and other clinical reactions for 2-3 weeks to evaluate attenuation of the mutant strain. At the end of this observation period surviving fish were challenged with a fixed dose of the wild type strain to evaluate efficacy of the mutant strain as a vaccine. Fish were observed for another 2 weeks.

For the wildtpe strain an inoculum was made of $2.25\times10^8$ cfu/ml. For the mutant strain this was $7.85\times10^8$ cfu/ml (about 3 times higher). Of these neat inoculums, 2-fold, 20-fold, 200-fold and 2000-fold dilutions were made for use in the attenuation study. The IP-challenge material contained $1.2\times10^6$ cfu/ml.

The results for the attenuation experiment are indicated in Table 10 (which shows the mortality at the end of the observation period). From this it becomes clear that the mutant strain is attenuated with respect to the wild-type strain: Although the neat inoculum for the mutant strain was three times higher in cfu's/ml, the mortality is significantly lower in the group that received the mutant strain. The results for the efficacy experiment are indicated in Table 11. Although no complete protection could be obtained, it is clear that the mutant provides significant protection (given the fact that in the control group 60 percent of the fish died during the observation period). Even in the group of fish that received the 2000-fold diluation, far less fish died because of the challenge with wild type *Nocardia seriolae*.

TABLE 10

| Mortality of fish (percentage) after administration of wild-type and mutant *N. seriolae* strain | | |
|---|---|---|
| | Wild-type | Mutant |
| 2-fold dilution | 80% | 50% |
| 20-fold dilution | 35% | 25% |
| 200-fold dilution | 5% | 0% |
| 2000-fold dilution | 0% | 0% |

TABLE 11

| Mortality of vaccinated fish (percentage) after challenge with wild-type *N. seriolae* | |
|---|---|
| 2-fold dilution | 10% |
| 20-fold dilution | 15% |
| 200-fold dilution | 15% |
| 2000-fold dilution | 20% |
| Control | 60% |

It has thus been shown that inactivation of a gene that encodes a protein involved in methylhexahydroindanedione propionate degradation, leads to an attenuated and protective vaccine strain in a second nocardioform actinomycete. This is further support for the fact that the invention is applicable over the whole range of nocardioform actinomycetes.

The invention claimed is:

1. A *Rhodococcus equi* bacterium derived from a strain as deposited with the Collection Nationale de Cultures de Micro-organismes of the Institut Pasteur at Paris France under nr. CNCM I-4108 or nr. CNCM I-4109.

2. A *Rhodococcus equi* bacterium of a strain as deposited with the Collection Nationale de Cultures de Micro-organismes of the Institut Pasteur at Paris France under nr. CNCM I-4108 or nr. CNCM I-4109.

3. A method of treating an animal to protect it against a disorder arising from an infection with a bacterium that belongs to the group of nocardioform actinomycetes having the ability to survive within macrophages of an animal, comprising administering to the animal a pharmaceutical composition comprising live bacteria of a nocardioform actinomycetes species, which live bacteria are attenuated by inactivation of a gene that encodes a protein involved in methylhexahydroindanedione propionate degradation.

* * * * *